US012708339B2

(12) United States Patent
Zhang et al.

(10) Patent No.: US 12,708,339 B2
(45) Date of Patent: Aug. 18, 2026

(54) DIGITAL X-RAY IMAGING METHOD AND APPARATUS

(71) Applicant: SHENZHEN MINDRAY BIO-MEDICAL ELECTRONICS CO., LTD., Shenzhen (CN)

(72) Inventors: Jiye Zhang, Shenzhen (CN); Zanchao Zhang, Shenzhen (CN); Yanpeng Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 236 days.

(21) Appl. No.: 18/598,915

(22) Filed: Mar. 7, 2024

(65) Prior Publication Data

US 2024/0341713 A1 Oct. 17, 2024

(30) Foreign Application Priority Data

Apr. 11, 2023 (CN) ......................... 202310426224.8

(51) Int. Cl.
*A61B 6/00* (2024.01)
*A61B 6/42* (2024.01)
*A61B 6/46* (2024.01)

(52) U.S. Cl.
CPC ............ *A61B 6/545* (2013.01); *A61B 6/4233* (2013.01); *A61B 6/4452* (2013.01); *A61B 6/465* (2013.01); *A61B 6/469* (2013.01); *A61B 6/5241* (2013.01)

(58) Field of Classification Search
None
See application file for complete search history.

(56) References Cited

U.S. PATENT DOCUMENTS 5,712,890 A 1/1998 Spivey et al.
6,895,076 B2 * 5/2005 Halsmer ................ A61B 6/544 378/98.12

(Continued)

FOREIGN PATENT DOCUMENTS

CN 102551742 A 7/2012
CN 104414660 A 3/2015

(Continued)

OTHER PUBLICATIONS

Extended European Search Report dated Aug. 20, 2025, issued in European Patent Application No. 24722098.1 (9 pages).

(Continued)

*Primary Examiner* — Thomas R Artman
(74) *Attorney, Agent, or Firm* — Sheppard Mullin Richter & Hampton LLP

(57) ABSTRACT

A method of digital X-ray imaging includes: displaying a body part of an object under examination on a display interface; determining a to-be-examined body position of the object from the body part in response to a selection instruction, obtaining digital X-ray images being stitched to generate a radiograph of the stitching body position and to form a stitching area between adjacent digital X-ray images; determining a radiographic parameter set of the stitching body position including travel points of an X-ray source and radiographic parameters; in response to a radiographing instruction, controlling the X-ray source to move to the travel points based on the radiographic parameter set, and emitting X-rays to the stitching body position based on the radiographic parameters at the travel points to obtain the digital X-ray images; and stitching the digital X-ray images to obtain the radiograph of the stitching body position.

15 Claims, 11 Drawing Sheets

(56) References Cited

U.S. PATENT DOCUMENTS

| | | | | |
|---|---|---|---|---|
| 10,098,598 | B2 * | 10/2018 | Lee | A61B 6/545 |
| 10,716,523 | B2 * | 7/2020 | Lee | A61B 6/469 |
| 10,835,196 | B2 * | 11/2020 | Wang | H04N 23/30 |
| 11,278,253 | B2 * | 3/2022 | Sato | A61B 6/588 |
| 11,957,495 | B2 * | 4/2024 | Lee | A61B 6/5241 |
| 2004/0247081 | A1 * | 12/2004 | Halsmer | A61B 6/5241 378/108 |
| 2016/0361035 | A1 * | 12/2016 | Lee | A61B 6/469 |
| 2019/0343479 | A1 * | 11/2019 | Sato | A61B 6/06 |
| 2020/0237332 | A1 * | 7/2020 | Wang | A61B 6/5241 |
| 2020/0345319 | A1 * | 11/2020 | Lee | A61B 6/5241 |
| 2023/0410292 | A1 * | 12/2023 | Schlueter | G06T 3/4038 |
| 2024/0237963 | A1 * | 7/2024 | Tsai | A61B 6/547 |
| 2024/0341712 | A1 * | 10/2024 | Zhang | A61B 6/465 |
| 2024/0341713 | A1 * | 10/2024 | Zhang | A61B 6/465 |
| 2026/0013819 | A1 * | 1/2026 | Zhang | A61B 6/0407 |

FOREIGN PATENT DOCUMENTS

| | | | |
|---|---|---|---|
| CN | 111815514 | A | 10/2020 |
| CN | 112535487 | A | 3/2021 |
| CN | 115914860 | A | 4/2023 |
| EP | 3135201 | A1 | 3/2017 |
| EP | 3996033 | A1 | 5/2022 |
| WO | 2009/149991 | A1 | 12/2009 |

OTHER PUBLICATIONS

PCT International Search Report and the Written Opinion mailed Jul. 29, 2024, issued in International Application No. PCT/CN2024/087332, with partial English machine translation (12 pages).

* cited by examiner controlling an X-ray source to emit X-rays to a stitching body position of an object under examination, and receiving the X-rays penetrating the stitching body position via a single detector to obtain a plurality of digital X-ray images in a first direction

100 stitching the plurality of digital X-rays images in the first direction along the first direction to obtain the radiograph of the stitching body position

110

FIG. 13 controlling the X-ray source to emit X-rays to the stitching body position of the object under examination, and receiving the X-rays penetrating the stitching body position via a single detector to obtain a plurality of digital X-rays images in the at least two directions respectively

stitching the plurality of digital X-rays images in the at least two directions along the at least two directions to obtain the radiograph of the stitching body position

DIGITAL X-RAY IMAGING METHOD AND APPARATUS

CROSS-REFERENCE TO RELATED APPLICATIONS

The application is based on and claims priority to and benefits of Chinese Patent Application No. 202310426224.8, filed on Apr. 11, 2023. The entire content of the above-referenced application is incorporated herein by reference.

TECHNICAL FIELD

The present disclosure relates to X-ray imaging, in particular to digital X-ray imaging methods and digital X-ray imaging apparatus.

BACKGROUND OF THE INVENTION

An X-ray imaging apparatus, such as a digital flat panel X-ray imaging apparatus, is a device that can reproduce X-ray radiographs by processing X-rays that have been penetrated a human body and then collected by an X-ray detector (such as a flat panel detector).

The flat panel detectors available are standardized product with certain specifications, such as size of 43 cm*43 cm, which may cause inconvenience in practical use.

SUMMARY OF THE INVENTION

Considering the above problem, digital X-ray imaging methods and digital X-ray imaging apparatus are provided by the present disclosure, as detailed below.

In accordance with a first aspect, a digital X-ray imaging method provided in some embodiments may include:

displaying a detectable body part of an object under examination on a display interface;

determining a to-be-examined body position of the object from the detectable body part in response to a selection instruction on the detectable body part, the to-be-examined body position comprising a stitching body position, the stitching body position being radiographed in a first direction to obtain a plurality of digital X-ray images, the plurality of digital X-ray images being stitched to generate a radiograph of the stitching body position and form a stitching area between adjacent digital X-ray images when stitching, and the first direction being a direction of a coronal axis or a sagittal axis of the object under examination;

acquiring at least one region of interest of the stitching body position;

determining a radiographic parameter set of the stitching body position, the radiographic parameter set comprising a plurality of travel points of an X-ray source and radiographic parameters about the X-ray source at the plurality of travel points, the radiographic parameter set allowing the at least one region of interest to be completely captured during digital X-ray imaging and to be kept outside the stitching area;

in response to a radiographing instruction on the stitching body position, controlling the X-ray source to move to the plurality of travel points along the first direction based on the radiographic parameter set, and emitting X-rays to the stitching body position for radiographing based on the radiographic parameters about the X-ray source at the plurality of travel points to obtain the plurality of digital X-ray images; and stitching the plurality of digital X-ray images in the first direction to obtain the radiograph of the stitching body position.

In some embodiments, the stitching body position may be a chest stitching position or an abdomen stitching position.

In some embodiments, the method may further comprise: in response to a radiographing instruction on the stitching body position, controlling a detector to move based on the radiographic parameter set to receive the X-rays emitted at the plurality of travel points by the X-ray source respectively so as to obtain the plurality of digital X-ray images;

or, receiving the X-rays emitted at the plurality of travel points by the X-ray source via a fixed detector to obtain the plurality of digital X-ray images.

In some embodiments, determining the radiographic parameter set of the stitching body position may comprise: determining the radiographic parameter set of the stitching body position based on the at least one region of interest.

In some embodiments, acquiring at least one region of interest of the stitching body position may comprise:

displaying a first image of the stitching body position on the display interface;

in response to a user operation, determining the at least one region of interest of the stitching body position on the first image of the stitching body position.

In some embodiments, determining the radiographic parameter set of the stitching body position may comprise:

according to the at least one region of interest determined on the first image, calculating a travel point and an X-ray exposure area both associated with the region of interest, so that any one region of interest is capable of being fully covered by a corresponding single X-ray exposure area which is capable of fully covering the stitching area for stitching; and acquiring the radiographic parameter set at least according to the travel point and the X-ray exposure area both associated with the region of interest.

In some embodiments, acquiring at least one region of interest of the stitching body position may comprise:

when receiving a trigger instruction to calibrate a region of interest, acquiring a travel point of the X-ray source and an irradiation field of an X-ray beam limiter under the trigger instruction so as to calibrate the at least one region of interest of the stitching body position;

In some embodiments, determining the radiographic parameter set of the stitching body position may comprise:

respectively taking the travel point of the X-ray source and the irradiation field of the X-ray beam limiter under the trigger instruction as a travel point and an X-ray exposure area both associated with the region of interest; and acquiring the radiographic parameter set at least according to the travel point and the X-ray exposure area both associated with the region of interest.

In some embodiments, acquiring the radiographic parameter set at least according to the travel point and the X-ray exposure area both associated with the region of interest may comprise:

according to the travel point and the X-ray exposure area both associated with the region of interest, determining whether there is a gap area in the stitching body position that is not covered by the X-ray exposure area associated with the region of interest, and when there is the gap area: acquiring the gap area;

determining a travel point and an X-ray exposure area both associated with the gap area, so as to fully cover the gap area without overlapping with any one region of interest; and acquiring the radiographic parameter set according to the travel point and the X-ray exposure area both associated with the region of interest and the travel point and the X-ray exposure area both associated with the gap area; and when there isn't the gap area: acquiring the radiographic parameter set according to the travel point and the X-ray exposure area both associated with the region of interest.

In accordance with a second aspect, a digital X-ray imaging method provided in some embodiments may include:

configuring a current digital imaging mode in response to a mode configuring instruction, the digital imaging mode comprising at least two of a first stitching mode, a second stitching mode and a third stitching mode, wherein the first stitching mode comprises radiographing a stitching body position along a direction of a coronal axis of an object under examination to obtain a plurality of digital X-ray images that are subsequently stitched to generate a radiograph of the stitching body position, the second stitching mode comprises radiographing a stitching body position along a direction of a sagittal axis of an object under examination to obtain a plurality of digital X-ray images that are subsequently stitched to generate a radiograph of the stitching body position, and the third stitching mode comprises radiographing a stitching body position along a direction of a vertical axis of an object under examination to obtain a plurality of digital X-ray images that are subsequently stitched to generate a radiograph of the stitching body position;

when the current digital imaging mode is the first stitching mode:

controlling an X-ray source to emit X-rays to a stitching body position of an object under examination to obtain a plurality of digital X-ray images in the direction of the coronal axis; and stitching the plurality of digital X-ray images in the direction of the coronal axis along the direction of the coronal axis to obtain the radiograph of the stitching body position;

when the current digital imaging mode is the second stitching mode:

controlling an X-ray source to emit X-rays to a stitching body position of an object under examination to obtain a plurality of digital X-ray images in the direction of the sagittal axis; and stitching the plurality of digital X-ray images in the direction of the sagittal axis along the direction of the sagittal axis to obtain the radiograph of the stitching body position; and when the current digital imaging mode is the third stitching mode:

controlling an X-ray source to emit X-rays to a stitching body position of an object under examination to obtain a plurality of digital X-ray images in the direction of the vertical axis; and stitching the plurality of digital X-ray images in the direction of the vertical axis along the direction of the vertical axis to obtain the radiograph of the stitching body position.

In some embodiments, the digital imaging mode may further include a fourth stitching mode, wherein the fourth stitching mode may include: radiographing a stitching body position along at least two directions of an object under examination to obtain a plurality of digital X-ray images that are subsequently stitched to generate a radiograph of the stitching body position, the at least two direction may include at least two of the direction of the coronal axis, the direction of the sagittal axis and the direction of the vertical axis of the object under examination; and when the current digital imaging mode is the fourth stitching mode:

controlling an X-ray source to emit X-rays to a stitching body position of an object under examination to obtain a plurality of digital X-ray images in the at least two directions; and stitching the plurality of digital X-ray images in the at least two directions along the at least two directions to obtain the radiograph of the stitching body position.

In some embodiments, the plurality of digital X-ray images in the at least two directions comprise a plurality of digital X-ray images in the direction of the coronal axis and a plurality of digital X-ray images in the direction of the vertical axis;

stitching the plurality of digital X-ray images in the at least two directions along the at least two directions to obtain the radiograph of the stitching body position may comprise:

stitching the plurality of digital X-ray images in the direction of the coronal axis along the direction of the coronal axis to obtain an intermediate stitching image, and stitching the intermediate stitching image and the plurality of digital X-ray images in the direction of the vertical axis along the direction of the vertical axis to obtain a radiograph of the stitching body position;

or, stitching the plurality of digital X-ray images in the direction of the vertical axis along the direction of the vertical axis to obtain an intermediate stitching image, and stitching the intermediate stitching image and the plurality of digital X-ray images in the direction of the coronal axis along the direction of the coronal axis to obtain a radiograph of the stitching body position.

In some embodiments, the method may further comprise: switching the current digital imaging mode among the stitching modes in response to a triggering of a mode switching button.

In accordance with a third aspect, a digital X-ray imaging method provided in some embodiments may include:

controlling an X-ray source to emit X-rays to a stitching body position of an object under examination and receiving the X-rays penetrating the stitching body position via a detector to obtain a plurality of digital X-ray images in a first direction that is a direction of a coronal axis or a sagittal axis of the object under examination; and stitching the plurality of digital X-ray images in the first direction along the first direction to obtain a radiograph of the stitching body position.

In some embodiments, the stitching body position is a chest stitching position or an abdomen stitching position.

In some embodiments, controlling an X-ray source to emit X-rays to a stitching body position of an object under examination and receiving the X-rays penetrating the stitching body position via a detector to obtain a plurality of digital X-ray images in the first direction may comprise:

controlling the X-ray source to move along the first direction to emit X-rays to the stitching body position at a plurality of travel points in the first direction, and controlling the detector to move along the first direction to receive the X-rays emitted at the plurality of travel points by the X-ray source respectively, or receiving the X-rays emitted at the plurality of travel points by the X-ray source via the detector at a preset travel point;

or, emitting the X-rays at a travel point multiple times by the X-ray source to the stitching body position, and controlling the detector to move along the first direction to receive the X-rays emitted multiple times by the X-ray source respectively, or receiving the X-rays emitted multiple times at said travel point by the X-ray source respectively via the detector at a preset travel point.

In some embodiments, the method may further comprise:

acquiring at least one region of interest of the stitching body position;

acquiring a radiographic parameter set of the stitching body position according to the at least one region of interest of the stitching body position, the radiographic parameter set comprising a plurality of travel points of the X-ray source and radiographic parameters about the X-ray source at the plurality of travel points, the radiographic parameter set allowing the at least one region of interest to be completely captured during digital X-ray imaging and to be kept outside a stitching area;

wherein the radiographic parameter set is configured to control the X-ray source to emit X-rays to the stitching body position of the object under examination, preferably, the radiographic parameter set is further configured to control the detector to receive the X-rays penetrating the stitching body position.

In accordance with a fourth aspect, a digital X-ray imaging method provided in some embodiments may include:

controlling an X-ray source to emit X-rays to a stitching body position of an object under examination, receiving the X-rays penetrating the stitching body position via a detector to obtain a plurality of digital X-ray images in at least two directions respectively; and stitching the plurality of digital X-ray images in at least two directions along the at least two directions to obtain a radiograph of the stitching body position.

In some embodiments, the plurality of digital X-ray images in at least two directions may comprise a plurality of digital X-ray images in the direction of the coronal axis and a plurality of digital X-ray images in the direction of the sagittal axis, or a plurality of digital X-ray images in the direction of the coronal axis and a plurality of digital X-ray images in the direction of the vertical axis, or a plurality of digital X-ray images in the direction of the sagittal axis and a plurality of digital X-ray images in the direction of the vertical axis.

In accordance with a fifth aspect, a digital X-ray imaging method provided in some embodiments may include:

obtaining a plurality of digital X-ray images of an object under examination;

selecting at least two digital X-ray images from the plurality of digital X-ray images in response to an image selection instruction, the at least two digital X-ray images having an overlapping area; and stitching the at least two digital X-ray images in response to a stitching instruction to obtain a stitched radiograph.

In some embodiments, the stitching instruction comprises at least one of a first stitching instruction, a second stitching instruction, a third stitching instruction and a fourth stitching instruction;

stitching the at least two digital X-ray images in a direction of a sagittal axis of the object under examination in response to the first stitching instruction;

stitching the at least two digital X-ray images in a direction of a coronal axis of the object under examination in response to the second stitching instruction;

stitching the at least two digital X-ray images in a direction of a vertical axis of the object under examination in response to the third stitching instruction; and stitching the at least two digital X-ray images in at least two directions in response to the fourth stitching instruction, the at least two directions comprising at least two of the direction of the coronal axis, the direction of the sagittal axis and the direction of the vertical axis of the object under examination.

In some embodiments, the method may further comprise: obtaining stitching parameters at least comprising at least one of width, brightness, contrast, sharpness, compression ratio, and compensation factor of the stitching area;

stitching the at least two digital X-ray images in response to a stitching instruction comprises: stitching the at least two digital X-ray images according to the stitching parameters.

In some embodiments, the method may further comprise: obtaining a region of interest in the at least two digital X-ray images, and determining whether there is an overlap between the region of interest and the stitching area, and when there is, issuing a prompt.

In some embodiments, the method may further comprise: displaying the at least two digital X-ray images and the stitched radiograph simultaneously.

In accordance with a sixth aspect, a digital X-ray imaging apparatus provided in some embodiments may include:

an X-ray source configured to emit X-rays to an object under examination;

a detector configured to receive the X-rays penetrating the object under examination;

a driving member configured to drive the X-ray source and/or the detector to move; and a processor configured to execute the method in any one of the embodiments mentioned herein.

With the digital X-ray imaging methods and the digital X-ray imaging apparatus mentioned in some embodiments above, a stitching body position can be radiographed and stitched in a first direction.

With the digital X-ray imaging methods and the digital X-ray imaging apparatus mentioned in some embodiments above, a region of interest in a stitching body position can be completely captured at one time during X-ray imaging, and be outside a stitched area in a stitched image.

BRIEF DESCRIPTION OF THE DRAWINGS

FIG. 1(*b*) is a schematic diagram of three standard planes and axes corresponding to the anatomical posture of a human body;

FIG. 13 is a flow chart of a digital X-ray imaging method in some embodiments;

FIG. 14 is a flowchart of a digital X-ray imaging method in some embodiments;

DETAILED DESCRIPTION

The present disclosure is further described in detail below through specific embodiments in combination with the drawings, wherein, similar elements in different embodiments adopt associated similar element labels. In the following embodiments, many details are described in order to make the application be better understood. However, those skilled in the art can easily realize that some features can be omitted in different cases or can be replaced by other elements, materials and methods. In some cases, some operations related to the present disclosure are not shown or described in the specification in order to avoid the core part of the present disclosure being overwhelmed by excessive descriptions, and for those skilled in the art, it is not necessary to describe these relevant operations in detail, they can completely understand the relevant operations according to the description in the specification and the general technical knowledge of the field.

In addition, the features, operations or characteristics described in the specification may be combined in any appropriate manner to form various embodiments. At the same time, the steps or actions described in the method may be sequenced or adjusted in a manner apparent to those skilled in the art. Therefore, the sequences in the specification and the drawings are intended to clearly describe an embodiment and are not meant to be a required sequence unless it is indicated otherwise that a sequence must be followed.

The serial numbers assigned to the parts in the present disclosure, such as "first", "second", etc., are only used to distinguish the described objects, and do not have any sequential or technical meaning. The terms "connect" and "couple" as mentioned in the present disclosure, unless otherwise specified, include direct and indirect connection (coupling).

Figure 1A:
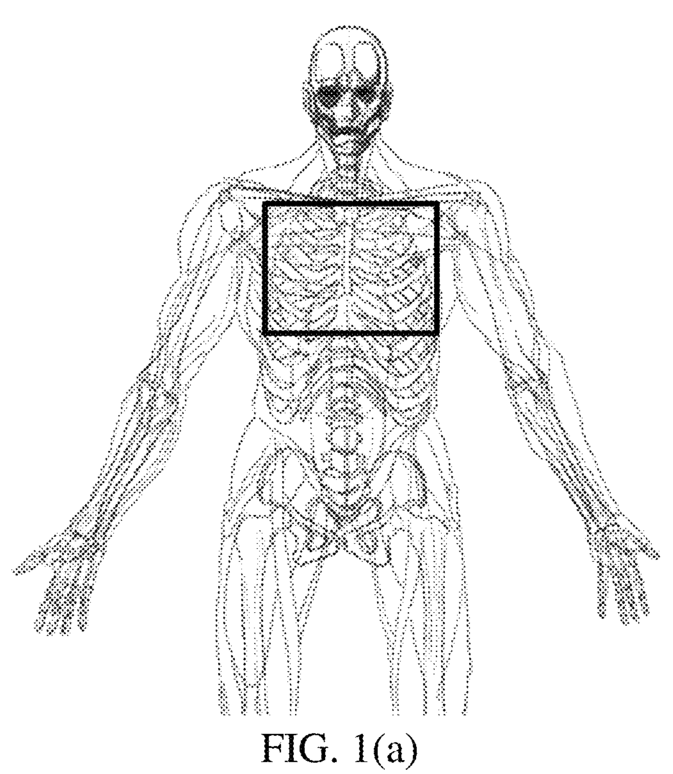
FIG. 1(*a*) is a schematic diagram of incomplete coverage of a flat panel detector when performing digital X-ray imaging on a chest.
Figure 1B:
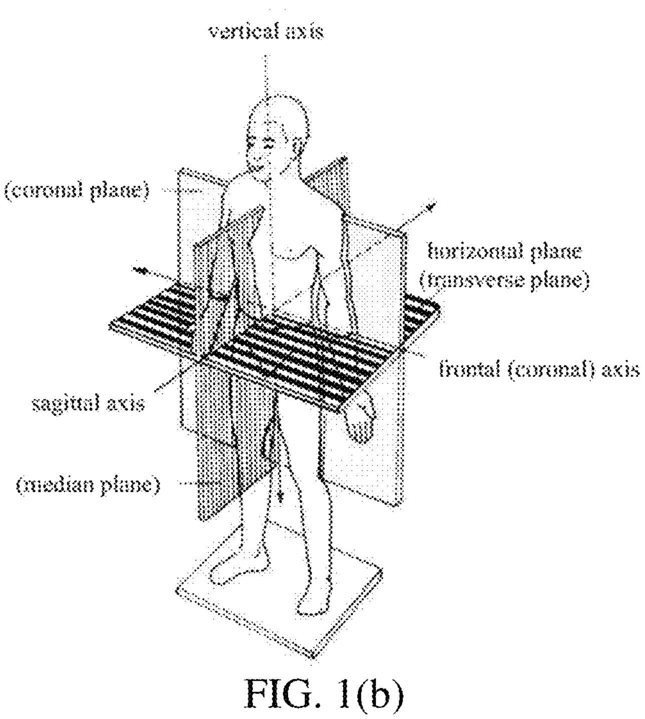

Referring to FIG. 1(*a*), the size of a flat panel detector is usually a fixed standard size. However, with the improvement of living standards, the number of patients with larger body size increases, and the probability of incomplete coverage of the flat panel detector may thus become larger. The applicant found that, for patients with larger body size, when performing X-ray imaging on their body parts such as chests, abdomens, the existing flat panel detector fails to fully cover the body parts being checked. The black thick-line rectangular box shown in FIG. 1 represents the schematic diagram the size range of the flat panel detector. Due to the relatively small number of patients with larger body size in clinical practice, technicians have not yet realized the problem and clinical demand for the problem of incomplete coverage of the patients' large transverse size, no relevant solution thus has been not proposed.

As used herein, the body part such as chest, abdomen are referred to as a stitching body position, and lateral radiography and stitching techniques are adopted in the present disclosure.

Additionally, three axes of a human body or an object under examination, namely coronal axis, sagittal axis, and vertical axis, are involved herein. FIG. 1(*b*) schematically shows three standard planes and three standard axes corresponding to an anatomical posture. When describing the azimuth axis or plane of the human body, terms such as upper, lower, front, rear, left and right it refers to are all based on the orientation of the anatomical posture of a person being described; wherein the anatomical posture is defined as follows: the person is upright with legs closed together, both upper limbs hanging down, eyes looking straight ahead, and both palms and both feet pointing forward. Specifically speaking, the vertical axis may refer to a longitudinal axis that runs through the human body or part thereof in an up-down direction and is perpendicular to a horizontal plane; the sagittal axis may refer to a horizontal axis that runs through the human body or part thereof in a front-rear direction and is perpendicular to a coronal plane; and the coronal axis, also known as a frontal axis, is a horizontal axis that runs through the human body or part thereof in a left-right direction and is perpendicular to a sagittal plane. There are also three sections of the human body and part thereof, including: the coronal plane (also known as a frontal plane) dividing the human body or part thereof vertically into two parts (front and rear parts) and being perpendicular to the sagittal axis; the sagittal plane dividing the human body or part thereof vertically into two parts (left and right parts) and being perpendicular to the coronal axis; and the horizontal plane (also known as a transverse plane) dividing the human body or part thereof into two parts (upper and lower parts) and being perpendicular to the vertical axis. The vertical plane passing through the sagittal suture within cranial bones may be referred to as a median sagittal plane or median plane, whereas other sagittal planes are parallel to the median sagittal plane.

Figure 2:
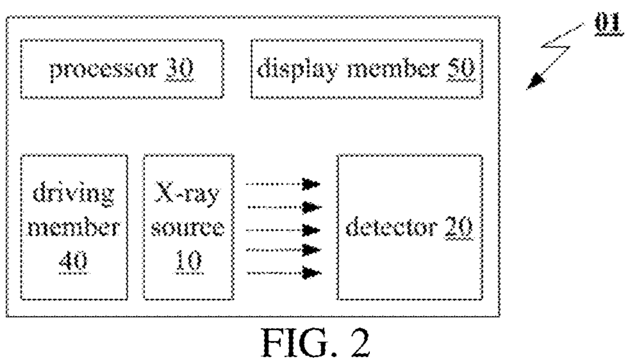
FIG. 2 is a schematic diagram of the structure of a digital X-ray imaging apparatus in some embodiments.

Referring to FIG. 2, in some embodiments, the digital X-ray imaging apparatus 01 may include an X-ray source 10, a detector 20 and a processor 30. Additionally or alternatively, in some embodiment, the digital X-ray imaging apparatus 01 may further include at least one of a driving member 40 and a display member 50. This will be illustrated in detailed below.

Figure 3:
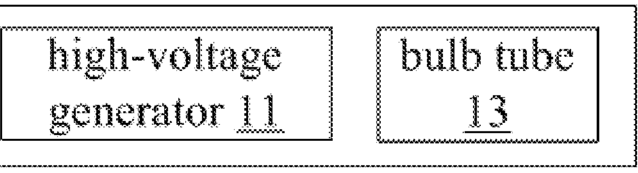
FIG. 3 is a schematic diagram of the structure of an X-ray source in some embodiments.

The X-ray source 10 may be configured to emit X-rays towards the object under examination, such as the to-be-examined body position. In some embodiments, the X-ray source 10 may be arranged relative to the detector 20 during operation. Referring to FIG. 3, the X-ray source 10 in some embodiments may include a high-voltage generator 11 and a bulb tube 13. The high-voltage generator 11 may be configured to provide a voltage, such as a kilovolt high voltage, to the bulb tube 13; and the bulb tube 13 may be configured to bombard electrons onto a target surface under the provided voltage from the high-voltage generator 11 to generate radiation including X-rays.

Figure 4:
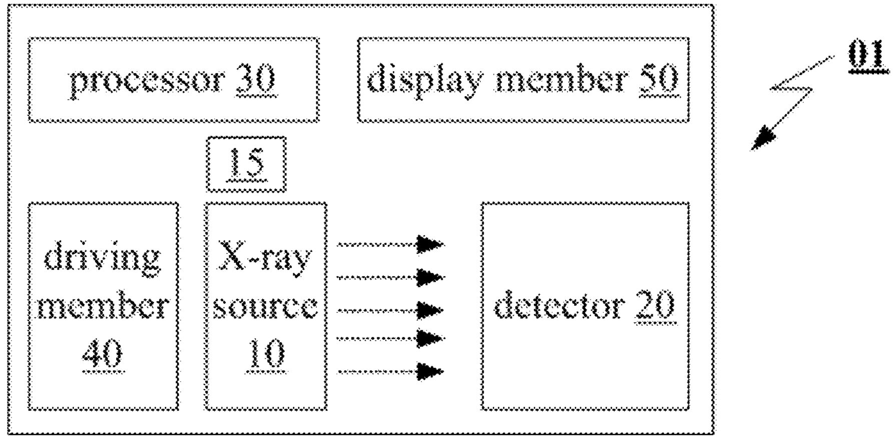
FIG. 4 is a schematic diagram of the structure of a digital X-ray imaging apparatus in some embodiments.

In some embodiments, referring to FIG. 4, the X-ray source 10 is provided with an X-ray beam limiter 15 configured to determine or simulate the radiating area of the X-ray source 10. The area irradiated by the X-ray beam limiter 15 may be referred to as an irradiation field.

Figure 5:
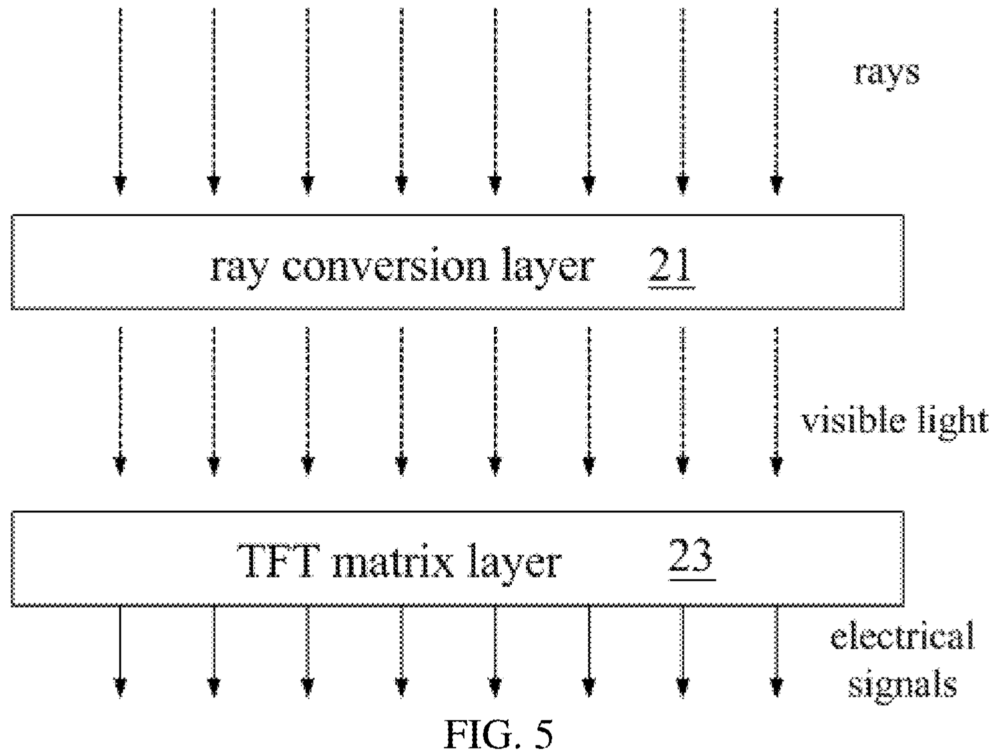
FIG. 5 is a schematic diagram of the structure of a detector in some embodiments.

The detector 20 may be configured to receive X-rays penetrating the object under examination, such as the to-be-examined body position. The detector 20 is a crucial component of the digital X-ray imaging apparatus 01 and plays a decisive role in ensuring high-quality imaging. It receives and converts the rays into electrical signals, thereby completing the acquisition of image information. Referring to FIG. 5, the detector 20 in some embodiments may include a ray conversion layer 21 and a TFT matrix layer 23. The ray conversion layer 21 may be configured to convert the rays into visible light. The ray conversion layer 21 may typically include a scintillation layer or a fluorescent layer for converting the rays into visible light. Taking the scintillation layer as an example, it may generally be made of scintillation materials, such as cesium iodide (CsI) or gadolinium oxysulfide (GOS). The TFT matrix layer 23 may be configured to sense the visible light converted by the ray conversion layer 21 and convert the visible light into electrical signals for acquiring image information.

In some embodiments, the detector 20 may be a flat panel detector.

As can be seen, the detector 20 is a ray-receiving unit in the digital X-ray imaging apparatus 01. The X-ray source 10 generates and emits X-rays which penetrate the to-be-examined body position of the object under examination and undergo attenuation, and the attenuated X-rays can be received by the detector 20; subsequently, the detector 20 receives the X-rays penetrating the to-be-examined body position of the object under examination for imaging. Specifically, the detector 20 captures and convert the X-rays into visible light before transforming them into electrical signals.

In some embodiments, there is one detector 20, that is, the digital X-ray imaging apparatus 01 may include only one detector 20.

In some embodiments, the driving member 40 may be configured to drive the X-ray source 10 to move.

In some embodiments, the driving member 40 may be configured to drive the detector 20 to move.

In some embodiments, the driving member 40 may be configured to drive the X-ray source 10 and the detector 20 to move, such as driving them to move synchronously.

The display member 50 may be configured to display, for example intermediate or final imaging results, and for example, a user interface, which will be further described below.

The above is some description of the digital X-ray imaging apparatus 01.

In some embodiments, the processor 30 may control the X-ray source 10 to emit X-rays to the stitching body position of the object under examination, and receive the X-rays penetrating the stitching body position via a detector (e.g., the detector 20) to obtain a plurality of digital X-ray images in a first direction. Subsequently, the processor 30 may stitch the plurality of digital X-ray images in the first direction to obtain a radiograph of the stitching body position.

In some embodiments, the processor 30 may control the X-ray source 10 (e.g. by regulating the driving member 40 to drive the X-ray source 10) to move along the first direction, and emit X-rays to the stitching body position at a plurality of travel points along the first direction; and the processor 30 may control the detector 20 (e.g. by regulating the driving member 40 to drive the detector 20) to move along the first direction to receive the X-rays emitted at the plurality of travel points by the X-ray source 10. It can be seen that in such an example, the X-ray source 10 and the detector 20 are moving during this multiple radiographing.

In some embodiments, the processor 30 may control the X-ray source 10 (e.g., by controlling the driving member 40 to drive the X-ray source 10) to move in the first direction and emit X-rays to the stitching body position at a plurality of travel points along the first direction; and the processor 30 may receive the X-rays emitted at the plurality of travel points by the X-ray source 10 at a preset point respectively. As can be seen, in such an example, the X-ray source 10 is moving while the detector 20 is fixed during this multiple radiographing.

In some embodiments, the processor 30 may emit X-rays multiple times to the stitching body position by the X-ray source 10 at a travel point and control the detector 20 (e.g., by controlling the driving member 40 to drive the detector 20) to move in the first direction to sequentially receive the X-rays emitted multiple times by the X-ray source 10. As can be seen that in such an example, the X-ray source 10 is fixed while the detector 20 is moving during this multiple radiographing.

In some embodiments, the processor 30 may emit X-rays multiple times to the stitching body position by the X-ray source 10 at a travel point, and the processor 30 may receive the X-rays emitted multiple times at the travel point by the X-ray source 10 via the detector 20 at a preset travel point. As can be seen that in such an example, the X-ray source 10 and the detector 20 are fixed during this multiple radiographing.

Figure 6:
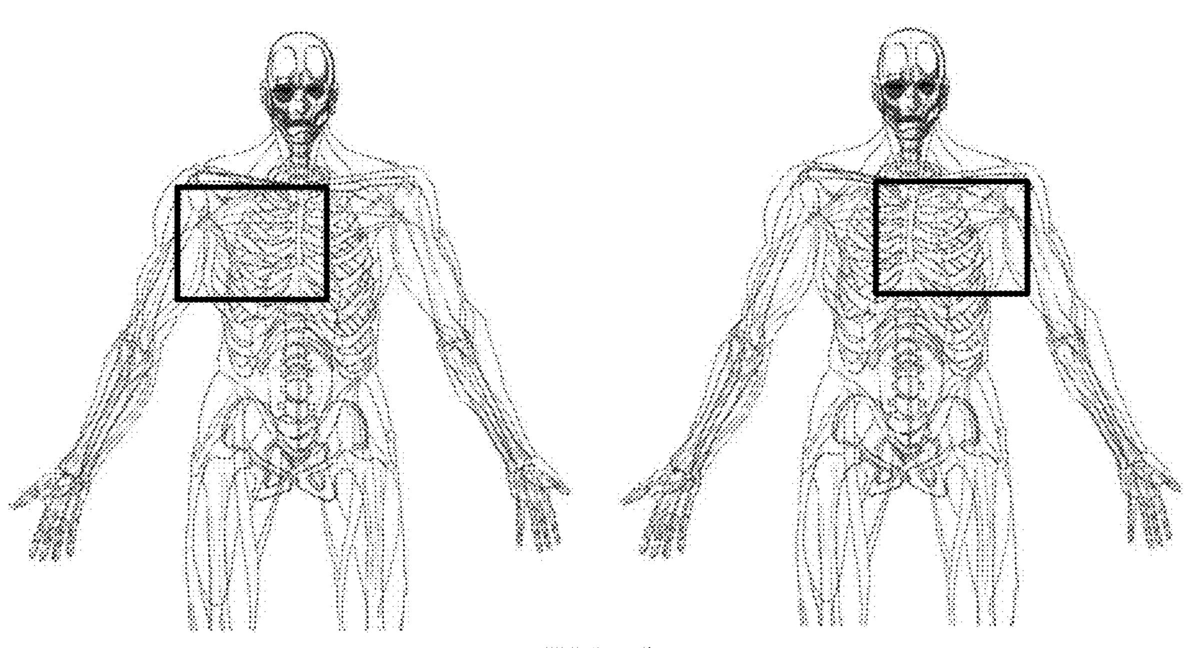
FIG. 6 is a schematic diagram of the structure of two digital X-ray images taken along the direction of coronal axis of the object under examination in some embodiments.

In some embodiments, the first direction may correspond to the direction of the coronal axis of the object under examination. Regardless of whether the object under examination is in an upright or prone position, the direction of the coronal axis of the object under examination may refer to a left-to-right or right-to-left direction of the object under examination. FIG. 6 illustrates an example where two digital X-ray images are captured along the direction of the coronal axis of the object under examination (from left to right). The two images have a certain overlapping area intended for easily stitching.

In some embodiments, the first direction may correspond to the direction of the sagittal axis of the object under examination. Regardless of whether the object under examination is in an upright or prone position, the direction of the sagittal axis of the object under examination may refer to a front-to-rear or rear-to-front direction of the object under examination.

In some embodiments, the stitching body position may be a chest stitching position, or an abdomen stitching position.

In some embodiments, the processor 30 may control the X-ray source 10 to emit X-rays to the stitching body position of the object under examination, receive the X-rays penetrating the stitching body position via a detector (e.g., the detector 20) to acquire a plurality of digital X-ray images in a second direction, and stitch the plurality of digital X-ray images in the second direction to obtain a radiograph of the stitching body position.

In some embodiments, the processor 30 may control the X-ray source 10 (e.g. by regulating the driving member 40 to drive the X-ray source 10) to move along the second direction, and emit X-rays to the stitching body position at a plurality of travel points in the second direction; and the processor 30 may control the detector 20 (e.g. by controlling the driving member 40 to drive the detector 20) to move in the second direction to receive the X-rays emitted at the plurality of travel points by the X-ray source 10. As can be seen, in such an example, the X-ray source 10 and the detector 20 are moving during this multiple radiographing.

In some embodiments, the processor 30 may control the X-ray source 10 (e.g., by regulating the driving member 40 to drive the X-ray source 10) to move along the second direction, and emit X-rays to the stitching body position at a plurality of travel points in the second direction; and the processor 30 may receive the X-rays emitted at the plurality of travel points by the X-ray source 10 at a preset travel point via the detector 20. As can be seen, in such an example, the X-ray source 10 is moving and the detector 20 is fixed during this multiple radiographing.

In some embodiments, the processor 30 may control the X-ray source 10 to emit X-rays multiple times to the stitching body position at a travel point, and control the detector 20 (e.g., by controlling the driving member 40 to drive the detector 20) to move along the second direction to subsequently receive the X-rays emitted multiple times by the X-ray source 10. It can be seen that in such an embodiment, the X-ray source 10 is fixed and the detector 20 is moving during this multiple radiographing.

In some embodiments, the processor 30 may emit X-rays to the stitching body position multiple times by the X-ray source 10 at a travel point, and subsequently the processor 30 may receive the X-rays emitted multiple times by the X-ray source 10 at the travel point via the detector 20 at a preset travel point. It can be seen that in such an example the X-ray source 10 and the detector 20 are fixed during this multiple radiographing.

In some embodiments, the second direction may correspond to the direction of the direction of the vertical axis of the object under examination. Regardless of whether the object under examination is in an upright or prone position, the direction of the vertical axis of the object under examination may refer to a top-to-bottom or bottom-to-top direction of the object under examination. For example, when the object under examination is in an upright position, the multiple radiographing may be performed, starting from the waist of the object under examination, from top to bottom to obtain a radiograph of the complete lower limb of the object under examination.

In some embodiments, the processor 30 may control the X-ray source 10 to emit X-rays to the stitching body position of the object under examination, and receive the X-rays penetrating the stitching body position via a detector (e.g. the detector 20) to obtain a plurality of digital X-ray images in the at least two directions; and the processor 30 may stitch the plurality of digital X-ray images in the at least two directions along the at least two directions to obtain a radiograph of the stitching body position.

In some embodiments, the plurality of digital X-ray images in the at least two directions may include a plurality of digital X-ray images in the direction of the coronal axis and a plurality of digital X-ray images in the direction of the sagittal axis, or a plurality of digital X-ray images in the direction of the coronal axis and a plurality of digital X-ray images in the direction of the vertical axis, or a plurality of digital X-ray images in the direction of the sagittal axis and a plurality of digital X-ray images in the direction of the vertical axis.

For example, the processor 30 may control the X-ray source 10 to emit X-rays to the stitching body position of the object under examination, and receive the X-rays penetrating the stitching body position via a detector (e.g. the detector 20) to obtain a plurality of digital X-ray images in the direction of the coronal axis and a plurality of digital X-ray images in the direction of the vertical axis; and the processor 30 may stitch in the directions of the coronal axis and the vertical axis the plurality of digital X-ray images in the direction of the coronal axis and the plurality of digital X-ray images in the direction of the vertical axis to obtain a radiograph of the stitching body position. In some specific embodiments, the processor 30 may stitch in the direction of the coronal axis the plurality of digital X-ray images in the direction of the coronal axis to obtain an intermediate stitching image, and stitch in the direction of the vertical axis the intermediate stitching image and the plurality of digital X-ray images in the direction of the vertical axis to obtain a digital X-ray image of the stitching body position. In some specific embodiments, the processor may stitch in the direction of the coronal axis the plurality of digital X-ray images in the direction of the vertical axis to obtain an intermediate stitching image, and stitch in the direction of the vertical axis the intermediate stitching image and the plurality of digital X-ray images in the direction of the coronal axis to obtain a digital X-ray image of the stitching body position.

In some embodiments, the radiographic manners and stitching modes in various directions mentioned above can be configured as corresponding stitching modes for users to choose. For example, in some embodiments, the digital X-ray imaging apparatus 01 may include at least two of a first stitching mode, a second stitching mode and a third stitching mode. Additionally, in some embodiments, the digital imaging mode may further include a fourth stitching mode. This will be illustrated in detailed below.

In some embodiments, the first stitching mode may include: radiographing a stitching body position along the direction of the coronal axis of the object under examination to obtain a plurality of digital X-ray images that are subsequently stitched to generate a radiograph of the stitching body position.

In some embodiments, the second stitching mode may comprise: radiographing the stitching body position along the direction of the sagittal axis of the object under examination to obtain a plurality of digital X-ray images that are subsequently stitched to generate a radiograph of the stitching body position.

In some embodiments, the third stitching mode may comprise: radiographing the stitching body position along a direction of a vertical axis of the object under examination to obtain a plurality of digital X-ray images that are subsequently stitched to generate a radiograph of the stitching body position.

In some embodiments, the fourth stitching mode may comprise: radiographing the stitching body position along at least two directions of the object under examination to obtain a plurality of digital X-ray images that are subsequently stitched to generate a radiograph of the stitching body position. The at least two direction may include at least two of the direction of the coronal axis, the direction of the sagittal axis and the direction of the vertical axis of the object under examination.

In some embodiments, the processor 30 may configure a current digital imaging mode in response to a mode configuring instruction.

When the current digital imaging mode is the first stitching mode: the processor 30 may control the X-ray source 10 emit X-rays to the stitching body position of the object under examination to obtain a plurality of digital X-ray images in the direction of the coronal axis; and the processor 30 may stitch the plurality of digital X-ray images in the direction of the coronal axis along the direction of the coronal axis to obtain the radiograph of the stitching body position. In some embodiments, the processor 30 may control the X-ray source 10 to emit X-rays to the stitching body position of the object under examination, and may receive the X-rays penetrating the stitching body position by one or more detectors. For example, when the processor 30 controls the X-ray source 10 to emit X-rays to the stitching body position of the object under examination and receives the X-rays penetrating the stitching body position via a detector 20, specifically, the processor 30 controls the X-ray source 10 to move along the direction of the coronal axis and emit X-rays to the stitching body position at a plurality of travel points in the direction of the coronal axis; and the processor 30 controls the detector 20 to move along the direction of the coronal axis to receive X-rays emitted at the plurality of travel points by the X-ray source respectively, or receives X-rays emitted at the plurality of travel points by the X-ray source 10 via a fixed detector 20 respectively.

When the current digital imaging mode is the second stitching mode: the processor 30 may control the X-ray source 10 to emit X-rays to the stitching body position of the object under examination to obtain a plurality of digital X-ray images in the direction of the sagittal axis; and the processor 30 may stitch the plurality of digital X-ray images in the direction of the sagittal axis along the direction of the sagittal axis to obtain the radiograph of the stitching body position. In some embodiments, the processor 30 controls the X-ray source 10 to emit X-rays to the stitching body position of the object under examination and receives the X-rays penetrating the stitching body position via one or more detectors. For example, when the processor 30 controls the X-ray source 10 to emit the stitching body position of the object under examination and receives the X-rays penetrating the stitching body position via a detector 20, specifically, the processor 30 controls the X-ray source 10 to move along the direction of the sagittal axis and emit X-rays to the stitching body position at a plurality of travel points along the direction of the sagittal axis; and the processor controls the detector 20 to move along the direction of the sagittal axis to respectively receive the X-rays emitted at the plurality of travel points by the X-ray source 10, or receives the X-rays emitted at the plurality of travel points by the X-ray source respectively via a fixed detector 20.

When the current digital imaging mode is the third stitching mode: the processor 30 may control the X-ray source to emit X-rays to the stitching body position of the object under examination to obtain a plurality of digital X-ray image in the direction of the vertical axis; and the processor 30 may stitch the plurality of digital X-ray images in the direction of the vertical axis along the direction of the vertical axis to obtain the radiograph of the stitching body position. In some embodiments, the processor 30 may control the X-ray source 10 to emit X-rays to the stitching body position of the object under examination and may receive the X-rays penetrating the stitching body position via one or more detectors. For example, when the processor 30 controls the X-ray source 10 to emit X-rays to the stitching body position of the object under examination and receives the X-rays penetrating the stitching body position via a detector 20, specifically, the processor 30 controls the X-ray source 10 to move along the direction of the vertical axis and emit the X-rays to the stitching body position at the plurality of travel points along the direction of the vertical axis; and the processor controls the detector 20 to move along the direction of the vertical axis to respectively receive the X-rays emitted at the plurality of travel points by the X-ray source 10, or it may receive the X-rays emitted at the plurality of travel points by the X-ray source 10 via a fixed detector 20.

When the current digital imaging mode is the fourth stitching mode: the processor 30 may control the X-ray source to emit X-rays to the stitching body position of the object under examination to obtain a plurality of digital X-ray images in at least two directions; and the processor 30 may stitch the plurality of digital X-ray images in at least two directions along the at least two directions to obtain the radiograph of the stitching body position. For example, when the plurality of digital X-ray images in at least two directions include a plurality of digital X-ray images in the direction of the coronal axis and a plurality of digital X-ray images in the direction of the vertical axis, the processor 30 stitches the plurality of digital X-ray image in the direction of the coronal axis along the direction of the coronal axis to obtain an intermediate stitching image, and subsequently, the processor 30 stitches the intermediate stitching image and the plurality of digital X-ray images in the direction of the vertical axis along the direction of the vertical axis to obtain the radiograph of the stitching body position; or, the processor 30 stitches the plurality of digital X-ray images in the direction of the vertical axis along the direction of the vertical axis to obtain an intermediate stitching image, and subsequently, the processor 30 stitches the intermediate stitching image and the plurality of digital X-ray images in the direction of the coronal axis along the direction of the coronal axis to obtain the radiograph of the stitching body position.

Figure 7:
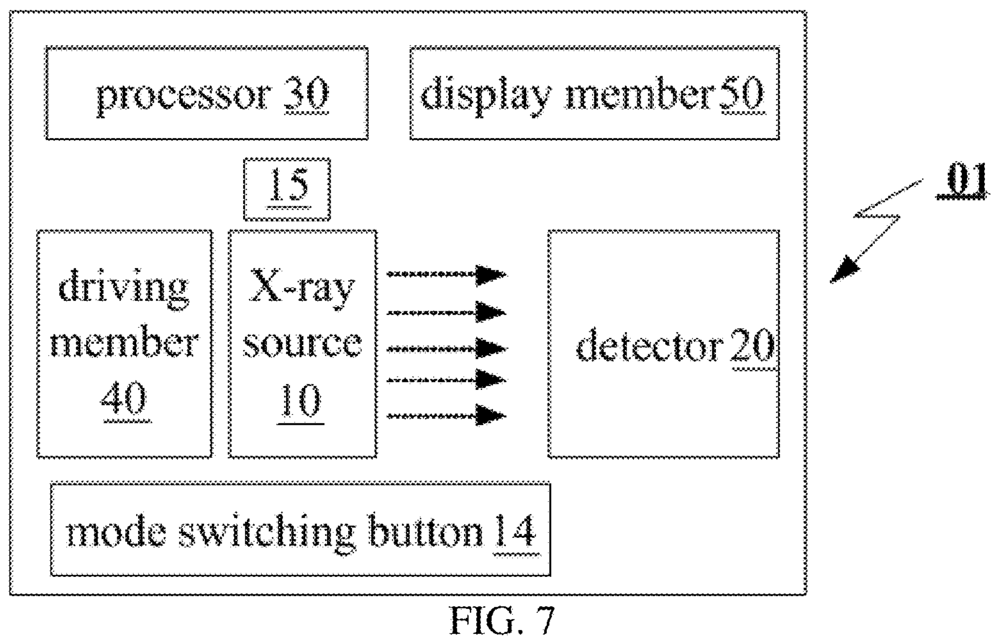
FIG. 7 is a schematic diagram of the structure of a digital X-ray imaging apparatus in some embodiments.

In some embodiments, referring to FIG. 7, a mode switching button 14 may be introduced. The mode switching button 14 may be a physical button or a virtual button. In response to the triggering of the mode switching button 14 the processor 13 may control switching among the digital imaging modes.

Figure 8:
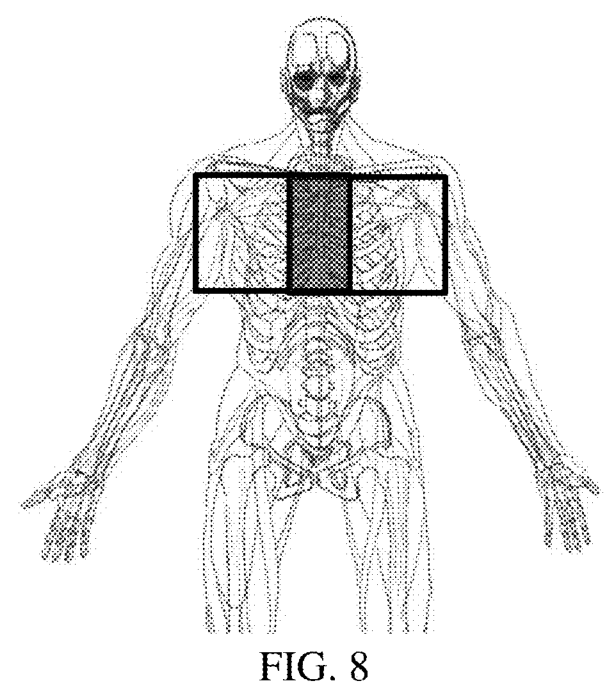
FIG. 8 is a schematic diagram of radiographing the stitching body position for a plurality of times and then making image stitching.

Referring to FIG. 8, the stitching body position is radiographed multiple times to obtain a plurality of images which are then stitched, wherein there is a certain overlapping area between adjacent images during stitching, which are referred to as a stitching area (see the area filled with gray diagonal line in the figure), so as to enable accurate matching and integration of adjacent images. The image effect of the stitching area formed by stitching is usually inferior to that of the non-stitched area (see the area not filled with gray diagonal line in the figure). The applicant found during practical research that when radiographing the stitching body position with X-rays, the region of interest is often located near the stitching area after stitching, which affects users' review and judgment of the area. For example, when radiographing the chest of a patient with X-rays, if the region of interest is the middle spine part of the patient, after radiographing the chest from left to right and the radiographed images are stitched, the middle spine part in the complete image after stitching may be located in the stitching area or partially overlapped with the stitching area, resulting in deformation and blurring of the middle spine part, affecting the users' grasp of the structure of the middle spine part through X-ray imaging. Based on this, the applicant proposes the digital X-ray imaging method disclosed herein, which enables the region of interest in the stitching body position can be completely radiographed at one time during X-ray imaging and is located outside the stitching area in the stitched image.

Figure 9:
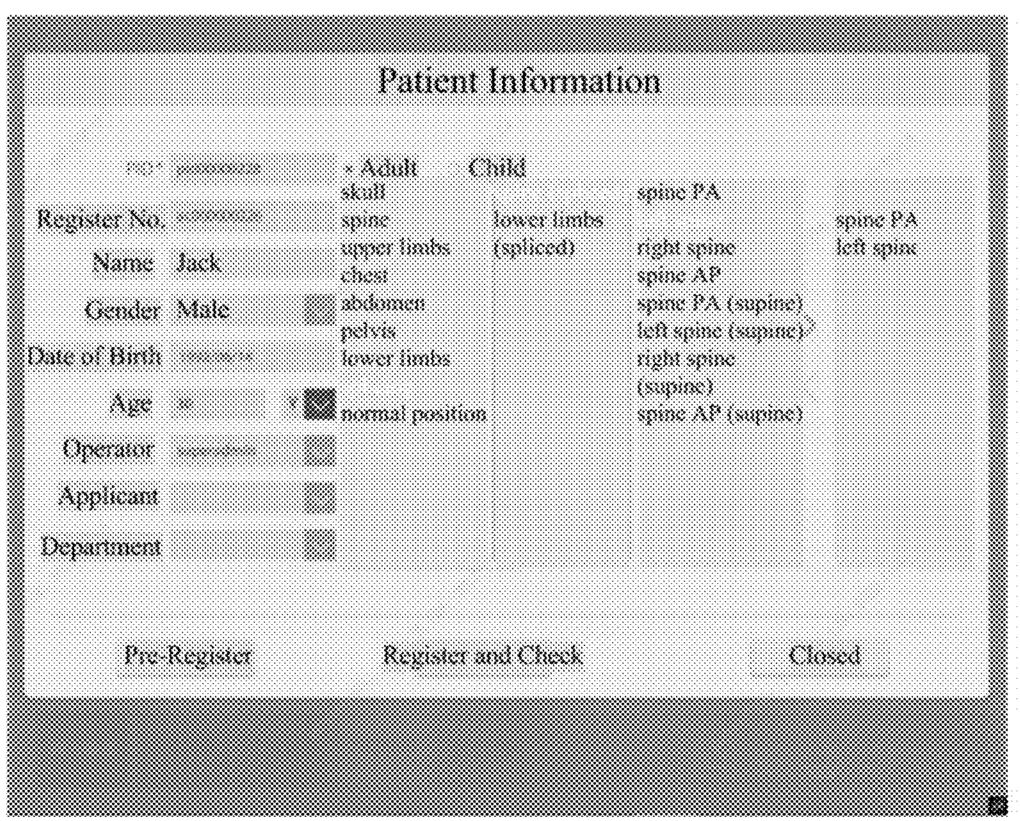
FIG. 9 is a schematic diagram of displaying and selecting a detectable body part on an interface in some embodiments.

In some embodiments, the display member 50 displays a detectable body part on an interface (for example, a first display interface which may be an information registration interface), such as an example as shown in FIG. 9. In response to a selection instruction on the detectable body part, the processor 30 may determine the to-be-examined body position of the object under examination from the detectable body part. In some embodiments, the to-be-examined body position may include a stitching body position which may be radiographed along a first direction to obtain a plurality of digital X-ray images that are then stitched to generate a radiograph of the stitching body position, wherein a stitching area may be formed between adjacent digital X-ray images during stitching. The processor 30 may obtain at least one region of interest of the stitching body position; and the processor 30 may determine a radiographic parameter set of the stitching body position which may include a plurality of travel points of the X-ray source 10 and radiographic parameters about the X-ray source at the plurality of travel points. The radiographic parameter set may allow at least one region of interest to be radiographed completely during digital X-ray imaging and be located outside the stitching area; in other words, the processor 30 may determine the radiographic parameter set of the stitching body position so that at least one region of interest can be radiographed completely during X-ray imaging and be located outside the stitching area, wherein the radiographic parameter set may comprise a plurality of travel points of the X-ray source 10 and radiographing parameters of the X-ray source 10 at the plurality of travel points. In some embodiments, the processor 30 may obtain the radiographic parameter set of the stitching body position according to the at least one region of interest.

In some embodiments, the first direction may be the direction of the coronal axis or the sagittal axis of the object under examination.

In some embodiments, the stitching body position may be a chest stitching position or an abdomen stitching position.

In response to a radiographing instruction on the stitching body position, the processor 30 may control the X-ray source 10 to move to a plurality of travel points along the first direction according to the radiographic parameter set, and emit X-rays to the stitching body position according to the radiographic parameters of the X-ray source 10 at the plurality of travel points to obtain a plurality of digital X-ray images. In some embodiments, in response to the radiographing instruction on the stitching body position, the processor 30 may further control a detector 20 to move according to the radiographic parameter set to receive the X-rays emitted by the X-ray source 10 at the plurality of travel points, respectively, to obtain digital X-ray images. In some embodiments, in response to the radiographing instruction on the stitching body position, the processor 30 may receive the X-rays emitted by the X-ray source 10 at the plurality of travel points via a fixed detector 20 to obtain digital X-ray images.

The processor 30 may stitch the plurality of digital X-ray images along the first direction to obtain the radiograph of the stitching body position; and in some embodiments, the display member 50 may display the stitched radiograph.

There are two key steps involved in the above process: obtaining the region of interest, and determining the radiographic parameter set. These are explained in detail below.

In some embodiments, the processor 30 may display a first image of the stitching body position on the display member 50 such as a stitching planning display; and in response to a user operation, the processor 30 may determine at least one region of interest within the stitching body position at the first image of the stitching body position.

Figure 10:
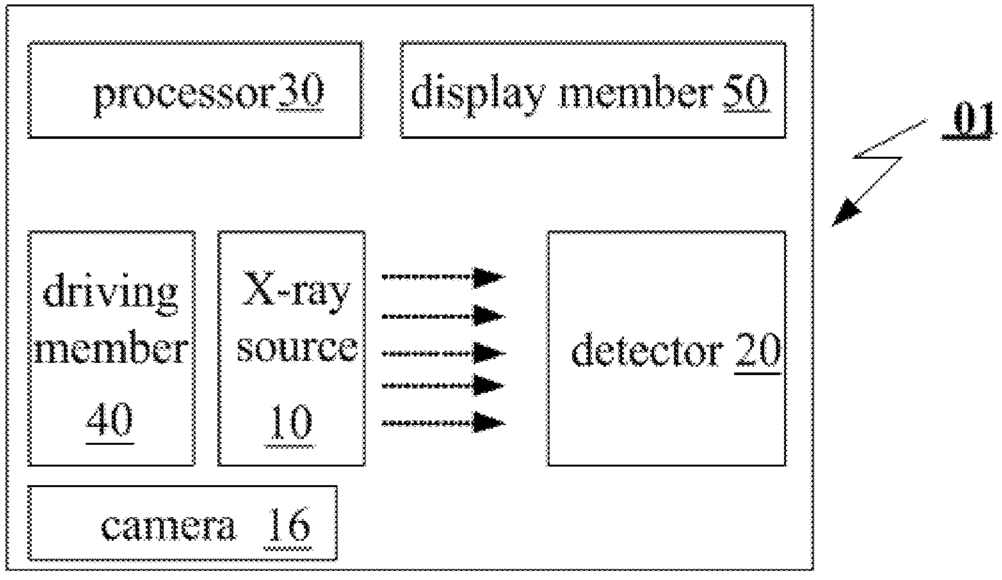
FIG. 10 is a schematic diagram of the structure of a digital X-ray imaging apparatus in some embodiments.
Figure 11:
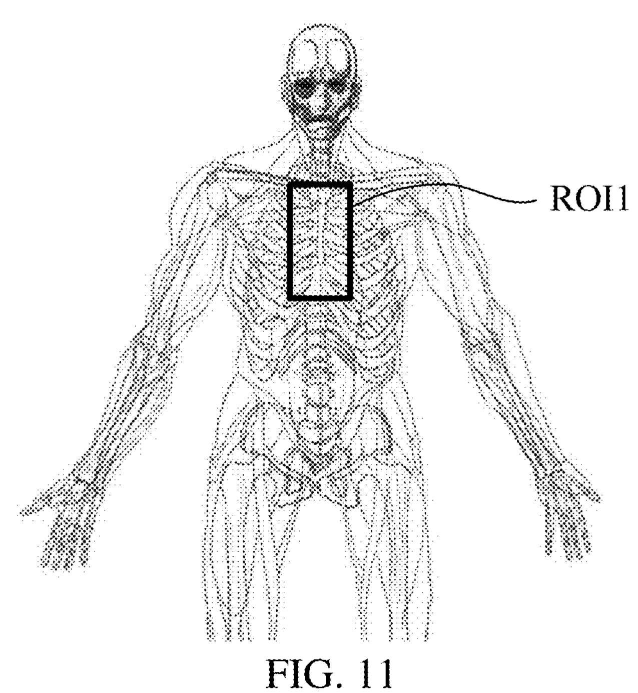
FIG. 11 is a schematic diagram of selecting a region of interest based on a first image in some embodiments.

For example, referring to FIG. 10, the digital X-ray imaging apparatus 01 may further include a camera 16 configured to image at least the stitching body position to generate the first image mentioned above. In some embodiments, the first image may be displayed on a display, and one or more regions of interest may be selected via a mouse or a touch operation. FIG. 11 shows an example where a region of interest is selected on the first image by a user, that is, the region of interest ROI 1 in the figure.

It is intuitive and convenient for users to select the region of interest on the image. After obtaining the region of interest, the following describes how to determine the radiographic parameter set for the stitching body position.

In some embodiments, the processor 30 may calculate the travel points and X-ray exposure areas related to the at least one region of interest determined in the first image, so that any region of interest can be completely covered by one of the individual X-ray exposure areas, and the X-ray exposure area can also completely cover the stitching area for stitching.

In some embodiments, the first image may include a depth-sensing image with three-dimensional spatial information about the stitching body position. In such case, the camera 16 is a depth-sensing camera. In some embodiments, the processor 30 may obtain spatial coordinates corresponding to the region of interest determined from the depth-sensing image, and calculate the travel points and X-ray exposure area both associated with the region of interest based on the spatial coordinates, so that any region of interest can be completely covered by one of the individual X-ray exposure areas and that the X-ray exposure area can cover the stitching area for stitching.

In some embodiments, the first image may include an optical image with two-dimensional spatial information about the stitching body position. In some embodiments, the processor 30 may obtain spatial coordinates corresponding to the region of interest according to at least one region of interest determined in the optical image and a pre-established mapping relationship between the optical image and spatial coordinates, and calculate the travel points and the X-ray exposure areas both associated with the region of interest according to the spatial coordinates corresponding to the region of interest, so that any region of interest can be completely covered by one of the individual X-ray exposure areas and the X-ray exposure area also completely can cover the stitching area for stitching.

Figure 12:
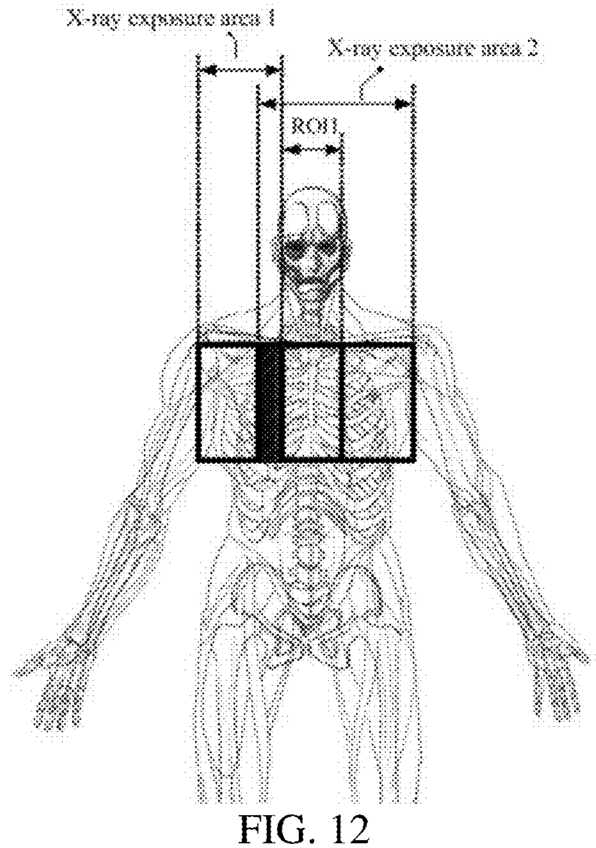
FIG. 12 is a schematic diagram of a radiographic parameter set obtained after selecting a region of interest based on the first image in some embodiments.

The processor 30 may obtain the radiographic parameter set at least according to the travel points and the X-ray exposure areas both associated with the region of interest. In some embodiments, the processor 30 may determine whether there is a gap area not covered by the X-ray exposure areas of the region of interest in the stitching body position according to the travel points and the X-ray exposure areas both associated with the region of interest. When there is the gap area not be covered, the processor 30 may obtain the gap area, as well as a travel point and an X-ray exposure area both associated with the gap area, which can be fully covered the gap area without overlapping with any region of interest; and the processor 30 may obtain the radiographic parameter set according to the travel point and the X-ray exposure area both associated with the region of interest and the travel point and the X-ray exposure area both associated with the gap area. When there isn't the gap area not be covered, the processor 30 may obtain the radiographic parameter set according to the travel points and the X-ray exposure areas both associated with the region of interest. For example, FIG. 12 is a schematic diagram of obtaining radiographic parameter set based on the region of interest selected from FIG. 11. The gray shaded area in the figure is the stitching area. It can be seen that the region of interest ROIl is completely covered by one of the individual X-ray exposure areas, and the X-ray exposure area also completely covers the stitching area used for stitching. The region of interest ROIl is not located in the stitching area.

The above is based on the description of obtaining the region of interest on the first image and further obtaining the radiographic parameter set.

From the perspective of user operation, in some embodiments, the display member 50 may display the detectable body part including the stitching body position on the interface. As mentioned above, the stitching body position may be radiographed in at least one direction to obtain a plurality of digital X-ray images. The radiograph of the stitching body position may be generated by stitching the plurality of digital X-ray images, and adjacent digital X-ray images may form a stitching area during stitching. In response to a selection instruction on the detectable body part, the processor 30 may determine the to-be-examined body position of the object under examination from the detectable body part. When the to-be-examined body position comprises the stitching body position, that is, the to-be-examined body position comprises the stitching body position, the processor 30 may control display the member 50 to display the first image of the stitching body position on the interface (such as the stitching planning display). In response to a user operation, the processor 30 may determine at least one region of interest of the stitching body position on the radiographed first image of the stitching body position; for example, the processor 30 may receive a box-selection operation from a user, control the display member 50 to display a corresponding selected box on the first image, and the region defined by the box may be determined as the region of interest. In some embodiments, the length of the selected box in the first direction, such as the direction of the coronal axis or the sagittal axis may be less than a first threshold. In some embodiments, the length of the selected box in the second direction, such as the direction of the vertical axis may be less than a second threshold. In some embodiments, the first threshold may be 27 cm to 25 cm. In some embodiments, the second threshold may be 9 cm to 7 cm. The processor 30 may determine the radiographic parameter set of the stitching body position according to at least one region of interest, such that the at least one region of interest can be completely radiographed during X-ray imaging and be located outside the stitching area. The radiographic parameter set may include a plurality of travel points of the X-ray source 10 and radiographic parameters of the X-ray source 10 at the plurality of travel points. In some embodiments, the processor 30 may calculate the travel point and X-ray exposure area related to the region of interest based on the at least one region of interest determined on the first image, so that any region of interest can be completely covered by one of the individual X-ray exposure areas and the X-ray exposure area also completely covers the stitching area for stitching. The processor 30 may obtain the radiographic parameter set at least based on the travel point and X-ray exposure area related to the region of interest. In some embodiments, the processor 30 may determine whether there is a gap area not covered by the X-ray exposure area related to the region of interest based on the travel point and X-ray exposure area related to the region of interest. When there is the gap area not be covered, the processor 30 may acquire the gap area, as well as the travel point and the X-ray exposure area both associated with the gap area, so as to completely cover the gap area without overlapping any region of interest; and the processor 30 may acquire the radiographic parameter set based on the travel point and the X-ray exposure area both associated with the region of interest and the travel point and the X-ray exposure area both associated with the gap area. When there isn't the gap area not be covered, the processor 30 may acquire the radiographic parameter set based on the travel point and X-ray exposure area related to the region of interest. Then, in response to the radiographing instruction, the processor 30 may control the X-ray source 10 to move to a plurality of travel points based on the radiographic parameter set, and may radiograph the stitching body position according to the radiographic parameters of the X-ray source 10 at the plurality of travel points to obtain a plurality of radiographs; subsequently, the processor 30 may stitch the plurality of radiographs to obtain a stitched radiograph that is displayed by the display member 50.

The above is a description from the perspective of user operation, explaining how to acquire the region of interest based on the first image and ultimately complete the capture and stitching of radiograph.

The following describes how to calibrate the region of interest by means of an X-ray beam limiter 15.

In some embodiments, when receiving a trigger instruction to calibrate a region of interest, the processor 30 may acquire the travel points of the X-ray source 10 and the irradiation field of the X-ray beam limiter 15 under the trigger instruction to calibrate at least one region of interest of the stitching body position. In some embodiments, the processor 30 may take a region corresponding to the irradiation field of the X-ray beam limiter 15 as the region of interest. In some embodiments, the processor 30 may determine a point of interest of the stitching body position according to the irradiation field of the X-ray beam limiter 15 under the trigger instruction, and then determine the region of interest based on the point of interest, for example, taking a region of preset size centered on the point of interest as the region of interest. In some embodiments, the length of the region of preset size in the first direction, for example, the direction of the coronal axis or the sagittal axis is less than a first threshold. In some embodiments, the length of the region of preset size in the second direction, for example, the direction of the vertical axis is less than a second threshold. In some embodiments, the first threshold is 27 cm to 25 cm. In some embodiments, the second threshold is 9 cm to 7 cm.

The X-ray source 10 may be moved by a user to drive the X-ray beam limiter 15 to move, and when the X-ray beam limiter 15 irradiates the region of interest, a trigger instruction may be sent to the processor 30 via the digital X-ray imaging apparatus 01 by the user to calibrate the region of interest.

The following describes how to determine the radiographic parameter set for the stitching body position after obtaining the region of interest.

In some embodiments, the processor 30 may take the travel points of the X-ray source 10 under the trigger instruction as the travel points related to the region of interest, and take the irradiation field of the X-ray beam limiter 15 under the trigger instruction as the X-ray exposure area related to the region of interest; then the processor 30 may obtain the radiographic parameter set at least according to the travel point and X-ray exposure area related to the region of interest. In some embodiments, the processor 30 may determine whether there is a gap area not covered by the X-ray exposure area related to the region of interest according to the travel point and X-ray exposure area related to the region of interest. When there is the gap area not covered, the processor 30 may obtain the gap area, as well as the travel point and the X-ray exposure area both associated with the gap area, so as to completely cover the gap area without overlapping with any region of interest; and the processor 30 may obtain the radiographic parameter set based on the travel point and the X-ray exposure area both associated with the region of interest and the travel point and the X-ray exposure area both associated with the gap area. When there is no gap area not covered, the processor 30 may obtain the radiographic parameter set based on the travel point and X-ray exposure area both associated with the region of interest.

The above is the description of how to calibrate the region of interest through the irradiation field of the X-ray beam limiter 15 and further to obtain the radiographic parameter set.

From the perspective of user operation, in some embodiments, the display member 50 may display the detectable body part including the stitching body position on the interface. As mentioned above, the stitching body position may be radiographed in at least one direction to obtain a plurality of digital X-ray images. The radiograph of the stitching body position may be generated by stitching the plurality of digital X-ray images, and adjacent digital X-ray images may form a stitching area during stitching. In response to a selection instruction on the detectable body part, the processor 30 may determine the to-be-examined body position of the object under examination from the detectable body part. When the to-be-examined body position comprises the stitching body position, that is, the to-be-examined body position comprises the stitching body position, the processor 30 may, when receiving the trigger instruction to calibrate the region of interest, obtain the travel points of the X-ray source 10 and the irradiation field of the X-ray beam limiter 15 under the trigger instruction to calibrate at least one region of interest of the stitching body position. In some embodiments, the processor 30 may determine the point of interest of the stitching body position according to the irradiation field of the X-ray beam limiter 15 under the trigger instruction, and then determine the region of interest according to the point of interest, for example, taking a region of preset size centered on the point of interest as the region of interest. In some embodiments, the length of the region of preset size in the first direction, for example, the direction of the coronal axis or the sagittal axis, is less than a first threshold. In some embodiments, the length of the region of preset size in the second direction, for example, the direction of the vertical axis, is less than a second threshold. In some embodiments, the first threshold is 27 cm to 25 cm. In some embodiments, the second threshold is 9 cm to 7 cm. The processor 30 may determine the radiographic parameter set of the stitching body position according to the at least one region of interest and to the travel points of the X-ray source 10 and the irradiation field of the X-ray beam limiter 15 under the trigger instruction, so that at least one region of interest can be fully radiographed during X-ray imaging and be located outside the stitching area. The radiographic parameter set may include a plurality of travel points of the X-ray source 10 and radiographic parameters of the X-ray source 10 at the plurality of travel points. In some embodiments, the processor 30 may take the travel points of the X-ray source 10 under the trigger instruction as the travel points related to the region of interest, and take the irradiation field of the X-ray beam limiter 15 under the trigger instruction as the X-ray exposure area related to the region of interest; then the processor 30 may obtain the radiographic parameter set at least according to the travel point and X-ray exposure area related to the region of interest. In some embodiments, the processor 30 may determine whether there is a gap area not covered by the X-ray exposure area related to the region of interest based on the travel point and X-ray exposure area related to the region of interest. When there is the gap area not be covered, the processor 30 may acquire the gap area, as well as the travel point and the X-ray exposure area both associated with the gap area, so as to completely cover the gap area without overlapping any region of interest; and the processor 30 may acquire the radiographic parameter set based on the travel point and the X-ray exposure area both associated with the region of interest and the travel point and the X-ray exposure area both associated with the gap area. When there isn't the gap area not be covered, the processor 30 may acquire the radiographic parameter set based on the travel point and X-ray exposure area related to the region of interest. Then, in response to the radiographing instruction, the processor 30 may control the X-ray source 10 to move to a plurality of travel points based on the radiographic parameter set, and may radiograph the stitching body position according to the radiographic parameters of the X-ray source 10 at the plurality of travel points to obtain a plurality of radiographs; subsequently, the processor 30 may stitch the plurality of radiographs to obtain a stitched radiograph that is displayed by the display member 50.

The above is a description from the perspective of user operation, explaining how to acquire the region of interest based on the irradiation field of the X-ray beam limiter 15 and ultimately complete the capture and stitching of radiograph.

In some implementations, it may also be possible to select images from the history of images that have been taken for stitching in the first direction.

In some embodiments, the processor 30 may obtain a plurality of digital X-ray images of the object under examination; then in response to an image selecting instruction, the processor 30 may select at least two digital X-ray images from the plurality of digital X-ray images. The at least two digital X-ray images may have an overlapping area, for example, the plurality of digital X-ray images may be obtained after radiographing, and then be displayed by the display member 50 so that the at least two digital X-ray images that are required can be selected by a user with a tool such as a mouse. The processor 30 may, in response to a stitching instruction, stitch the at least two digital X-ray images to obtain a stitched radiograph.

In some embodiments, the processor 30 may also obtain stitching parameters at least comprising at least one of width, brightness, contrast, sharpness, compression ratio, and compensation factor of the stitching area; accordingly, the processor 30 may stitch the at least two digital X-ray images based on the stitching parameters.

In some embodiments, the processor 30 may acquire the region of interest in the at least two digital X-ray images, and determine whether there is an overlap between the region of interest and the stitching area, and when there is the overlap, a prompt may be issued. The acquisition of the region of interest is described above and will not be repeated here.

In some embodiments, the display member 50 may display the at least two digital X-ray images and the stitched radiograph simultaneously.

In some embodiments of the present application, a digital X-ray imaging method is also proposed, which can be applied to the digital X-ray imaging apparatus 01 disclosed in some embodiments of the present application. This is described in detail below.

Referring to FIG. 13, the digital X-ray imaging method in some embodiments may include the following steps:

Step 100: controlling an X-ray source 10 to emit X-rays to a stitching body position of an object under examination, and receiving the X-rays penetrating the stitching body position via a single detector (e.g., the detector 20) to obtain a plurality of digital X-ray images in a first direction.

In some embodiments, the X-ray source 10 may be controlled to move (e.g. the X-ray source 10 may be driven by controlling a driving member 40) along the first direction and emit the X-rays at a plurality of travel points in the first direction to the stitching body position in step 100; and the detector 20 may be move (e.g. the detector 20 may be driven by controlling the driving member 40) along the first direction to receive the X-rays emitted at the plurality of travel points by the X-ray source 10 in step 100. As can be seen, in such embodiments, the X-ray source 10 and the detector 20 may be moving during the multiple radiographing.

In some embodiments, the X-ray source 10 may be controlled to move (e.g., the X-ray source 10 may be driven by controlling the driving member 40) in the first direction and emit the X-rays at the plurality of travel points in the first direction to the stitching body position in step 100; and the X-rays emitted at the plurality of travel points by the X-ray source 10 via the detector 20 at a preset travel point in step 100. As can be seen that, in such embodiments, the X-ray source 10 may be moved and the detector 20 may be fixed during the multiple radiographing.

In some embodiments, the X-ray source 10 may emit X-rays multiple times at a travel point to the stitching body position and the detector 20 may be controlled to move (e.g., the detector 20 may be driven by controlling the driving member 40) along the first direction to receive the X-rays emitted multiple times by the X-ray source 10 respectively in step 100. As can be seen that, in such embodiments, the X-ray source 10 may be fixed and the detector 20 may be moved during the multiple radiographing.

In some embodiments, the X-rays may be emitted multiple times at a travel point by the X-ray source 10 to the stitching body position in step 100, and the X-rays emitted multiple times at the travel point by the X-ray source 10 may be received respectively by the detector 20 in step 100. As can be seen that, in such embodiments, the X-ray source 10 and the detector 20 may be fixed during the multiple radiographing.

In some embodiments, the first direction may be the direction of the coronal axis of the object under examination. FIG. 6 illustrates an example where two digital X-ray images are captured along the direction of the coronal axis of the object under examination. The two digital X-ray images have a certain overlapping area intended for easily stitching.

In some embodiments, the first direction may correspond to the direction of the sagittal axis of the object under examination.

In some embodiments, the stitching body position may be a chest stitching position, or an abdomen stitching position.

Step 110: stitching the plurality of digital X-rays images in the first direction along the first direction to obtain the radiograph of the stitching body position.

Referring to FIG. 14, the digital X-ray imaging method in some embodiments may include the following steps:

Step 120: controlling the X-ray source 10 to emit X-rays to the stitching body position of the object under examination, and receiving the X-rays penetrating the stitching body position via a single detector (e.g., the detector 20) to obtain a plurality of digital X-rays images in the at least two directions respectively.

Step 130: stitching the plurality of digital X-rays images in the at least two directions along the at least two directions to obtain the radiograph of the stitching body position.

In some embodiments, the plurality of digital X-ray images in at least two directions may comprise a plurality of digital X-ray images in the direction of the coronal axis and a plurality of digital X-ray images in the direction of the sagittal axis, or a plurality of digital X-ray images in the direction of the coronal axis and a plurality of digital X-ray images in the direction of the vertical axis, or a plurality of digital X-ray images in the direction of the sagittal axis and a plurality of digital X-ray images in the direction of the vertical axis.

For example, the X-ray source 10 may be controlled to emit the X-rays to the stitching body position of the object under examination, and the detector (e.g., the detector 20) may be used to receive the X-rays penetrating the stitching body position, so as to obtain a plurality of digital X-ray images in the direction of the coronal axis and a plurality of digital X-ray images in the direction of the vertical axis in step 120. The plurality of digital X-ray images in the direction of the coronal axis and the plurality of digital X-ray images in the direction of the vertical axis may be stitched along the directions of the coronal axis and the vertical axis to obtain the radiograph of the stitching body position. In some embodiments, in step 130, the plurality of digital X-ray images in the direction of the coronal axis may be stitched in the direction of the coronal axis to obtain an intermediate stitching image; then the intermediate stitching image and the plurality of digital X-ray images in the direction of the vertical axis may be stitched along the direction of the vertical axis to obtain the digital X-rays image of the stitching body position. In some embodiments, in step 130, the plurality of digital X-ray images in the direction of the vertical axis may be stitched along the direction of the coronal axis to obtain an intermediate stitching image; then, the intermediate stitching image and the plurality of digital X-ray images in the direction of the coronal axis may be stitched along the direction of the vertical axis to obtain the digital X-ray image of the stitching body position.

Figure 15:
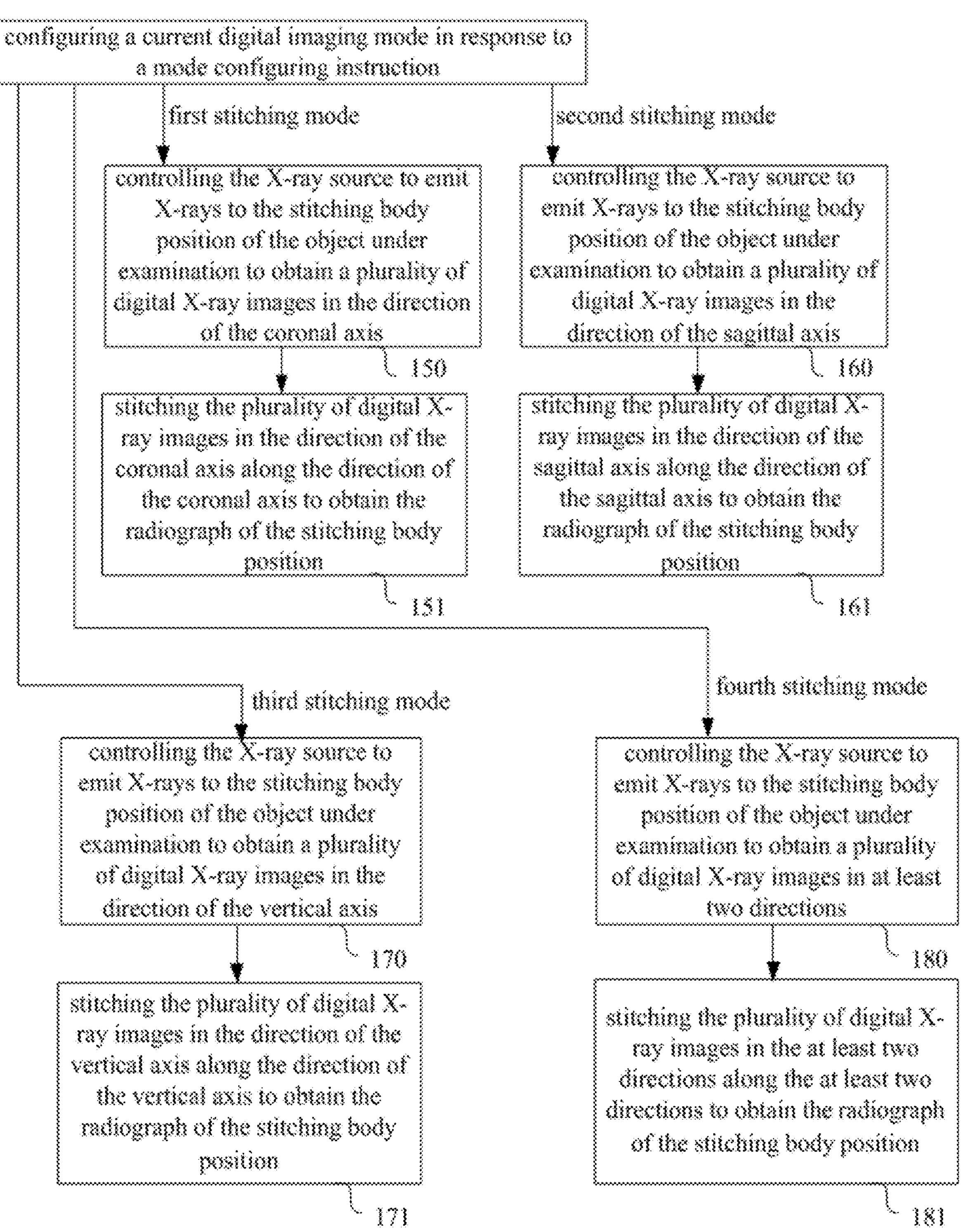
FIG. 15 is a flowchart of a digital X-ray imaging method in some embodiments.

Referring to FIG. 15, the digital X-ray imaging method in some embodiments may include the following steps:

Step 140: configuring a current digital imaging mode in response to a mode configuring instruction. In some embodiments, a mode switching button 14 may be introduced. The mode switching button 14 may be a physical button or a virtual button. In response to the triggering of the mode switching button 14, the digital imaging modes may be controlled to be switched.

In some embodiments, the digital imaging mode may include at least two of a first stitching mode, a second stitching mode, and a third stitching mode. In some embodiments, the digital imaging mode may also include a fourth stitching mode. This will be explained in detail below.

In some embodiments, the first stitching mode may include: radiographing a stitching body position along the direction of the coronal axis of the object under examination to obtain a plurality of digital X-ray images that are subsequently stitched to generate a radiograph of the stitching body position.

In some embodiments, the second stitching mode may comprise: radiographing the stitching body position along the direction of the sagittal axis of the object under examination to obtain a plurality of digital X-ray images that are subsequently stitched to generate a radiograph of the stitching body position.

In some embodiments, the third stitching mode may comprise: radiographing the stitching body position along a direction of a vertical axis of the object under examination to obtain a plurality of digital X-ray images that are subsequently stitched to generate a radiograph of the stitching body position.

In some embodiments, the fourth stitching mode may comprise: radiographing the stitching body position along at least two directions of the object under examination to obtain a plurality of digital X-ray images that are subsequently stitched to generate a radiograph of the stitching body position. The at least two direction may include at least two of the direction of the coronal axis, the direction of the sagittal axis and the direction of the vertical axis of the object under examination.

When the current digital imaging mode is the first stitching mode: the X-ray source 10 may be controlled to emit X-rays to the stitching body position of the object under examination to obtain a plurality of digital X-ray images in the direction of the coronal axis in step 150; and the plurality of digital X-ray images in the direction of the coronal axis may be stitched along the direction of the coronal axis to obtain the radiograph of the stitching body position in step 151. In some embodiments, the X-ray source 10 may be controlled to emit X-rays to the stitching body position of the object under examination, and one or more detectors may be used to receive the X-rays penetrating the stitching body position in step 150. For example, when the X-ray source 10 is controlled to emit X-rays to the stitching body position of the object under examination and the detector 20 may be used to receive the X-rays penetrating the stitching body position in step 150, specifically, the X-ray source 10 may be controlled to move along the direction of the coronal axis and emit the X-rays to the stitching body position at a plurality of travel points in the direction of the coronal axis in step 150; and the detector 20 may be controlled to move along the direction of the coronal axis to receive X-rays emitted at the plurality of travel points by the X-ray source respectively, or a fixed detector 20 may be used to receive the X-rays emitted at the plurality of travel points by the X-ray source 10 respectively.

When the current digital imaging mode is the second stitching mode: the X-ray source 10 may be controlled to emit X-rays to the stitching body position of the object under examination to obtain a plurality of digital X-ray images in the direction of the sagittal axis in step 160; and the plurality of digital X-ray images in the direction of the sagittal axis may be stitched along the direction of the sagittal axis to obtain the radiograph of the stitching body position in step 161. In some embodiments, the processor 30 controls the X-ray source 10 to emit X-rays to the stitching body position of the object under examination and receives the X-rays penetrating the stitching body position via one or more detectors. For example, when the X-ray source 10 is controlled to emit the stitching body position of the object under examination and the detector 20 receives the X-rays penetrating the stitching body position in step 160, specifically, the X-ray source 10 may be controlled to move along the direction of the sagittal axis and emit X-rays to the stitching body position at a plurality of travel points in the direction of the sagittal axis; and the detector 20 may be controlled to move along the direction of the sagittal axis to respectively receive the X-rays emitted at the plurality of travel points by the X-ray source 10, or a fixed detector 20 may receive the X-rays emitted at the plurality of travel points by the X-ray source respectively.

When the current digital imaging mode is the third stitching mode: the X-ray source may be controlled to emit X-rays to the stitching body position of the object under examination to obtain a plurality of digital X-ray images in the direction of the vertical axis in step 170; and the plurality of digital X-ray images in the direction of the vertical axis may be stitched along the direction of the vertical axis to obtain the radiograph of the stitching body position in step 171. In some embodiments, the processor 30 may control the X-ray source 10 to emit X-rays to the stitching body position of the object under examination and may receive the X-rays penetrating the stitching body position via one or more detectors. For example, when the X-ray source 10 is controlled to emit X-rays to the stitching body position of the object under examination and a detector 20 is used to receive the X-rays penetrating the stitching body position in step 170, specifically, the X-ray source 10 is controlled to move along the direction of the vertical axis and emit the X-rays to the stitching body position at the plurality of travel points along the direction of the vertical axis in step 170; and the detector 20 is controlled to move along the direction of the vertical axis to respectively receive the X-rays emitted at the plurality of travel points by the X-ray source 10, or a fixed detector 20 may be used to receive the X-rays emitted at the plurality of travel points by the X-ray source 10.

When the current digital imaging mode is the fourth stitching mode: the X-ray source may be controlled to emit X-rays to the stitching body position of the object under examination to obtain a plurality of digital X-ray images in at least two directions in step 180; and the plurality of digital X-ray images in at least two directions may be stitched along the at least two directions to obtain the radiograph of the stitching body position in step 181. For example, the plurality of digital X-ray images in at least two directions include a plurality of digital X-ray images in the direction of the coronal axis and a plurality of digital X-ray images in the direction of the vertical axis; the plurality of digital X-ray images in the direction of the coronal axis may be stitched along the direction of the coronal axis to obtain an intermediate stitching image in step 181, and subsequently, the intermediate stitching image and the plurality of digital X-ray images in the direction of the vertical axis may be stitched along the direction of the vertical axis to obtain the radiograph of the stitching body position in step 181; or, the plurality of digital X-ray image in the direction of the vertical axis may be stitched along the direction of the vertical axis to obtain an intermediate stitching image in step 181, and subsequently, the intermediate stitching image and the plurality of digital X-ray images in the direction of the coronal axis may be stitched along the direction of the coronal axis to obtain the radiograph of the stitching body position in step 181.

Figure 16:
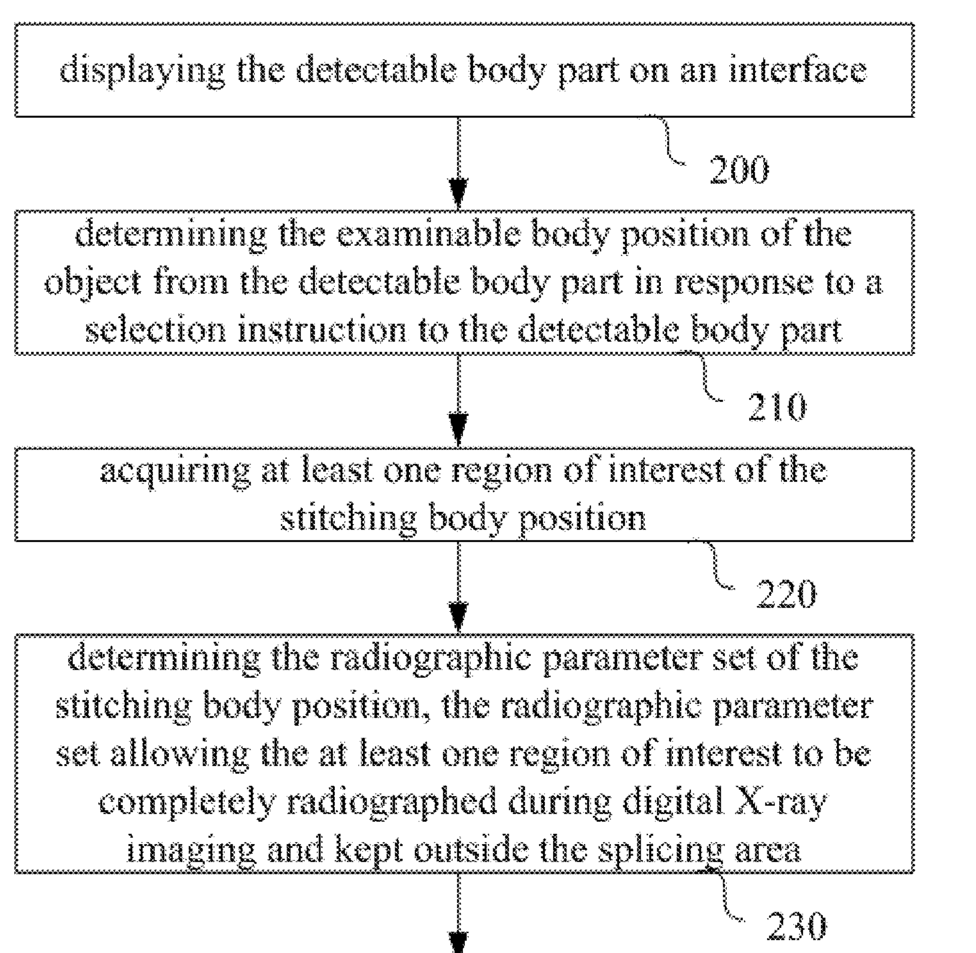
FIG. 16 is a flowchart of a digital X-ray imaging method in some embodiments.

Referring to FIG. 16, the digital X-ray imaging method in some embodiments may include the following steps:

Step 200: displaying the detectable body part on an interface (for example, a first display interface which may be an information registration interface), such as an example as shown in FIG. 9.

Step 210: determining the to-be-examined body position of the object from the detectable body part in response to a selection instruction on the detectable body part. In some embodiments, the to-be-examined body position may include a stitching body position which may be radiographed along the first direction to obtain a plurality of digital X-ray images which may be stitched to generate the radiograph of the stitching body position, and there is a stitching area formed between adjacent digital X-ray images during stitching.

Step 220: acquiring at least one region of interest of the stitching body position.

Step 230: determining the radiographic parameter set of the stitching body position. The radiographic parameter set may include a plurality of travel points of the X-ray source 10 and radiographic parameters about the X-ray source at the plurality of travel points. The radiographic parameter set may allow the at least one region of interest to be completely radiographed during digital X-ray imaging and be located outside the stitching area. In other words, the radiographic parameter set of the stitching body position may be determined in step 230 so that at least one region of interest may be completely radiographed during digital X-ray imaging and be located outside the stitching area. The radiographic parameter set may include a plurality of travel points of the X-ray source 10 and radiographic parameters of the X-ray source 10 at the plurality of travel points. In some embodiments, the radiographic parameter set of the stitching body position may be obtained based on the at least one region of interest in step 230.

In some embodiments, the first direction may be the direction of the coronal axis or the direction of the sagittal axis of the object under examination.

In some embodiments, the stitching body position may be a chest stitching position or an abdomen stitching position.

Step 240: in response to a radiographing instruction on the stitching body position, controlling the X-ray source 10 to move to a plurality of travel points along the first direction according to the radiographic parameter set, and emit X-rays to the stitching body position according to the radiographic parameters of the X-ray source 10 at the plurality of travel points to obtain a plurality of digital X-ray images. In some embodiments, in response to the radiographing instruction on the stitching body position, a detector 20 may also be controlled to move according to the radiographic parameter set to receive the X-rays emitted by the X-ray source 10 at the plurality of travel points, respectively, to obtain digital X-ray images in step 240. In some embodiments, in response to the radiographing instruction on the stitching body position, a fixed detector 20 may be used to receive the X-rays emitted by the X-ray source 10 at the plurality of travel points via to obtain digital X-ray images in step 240.

Step 250: stitching the plurality of digital X-ray images in the first direction to obtain the radiograph of the stitching body position.

The following will explain how to obtain the region of interest and how to obtain the radiographic parameter set based on the region of interest.

In some embodiments, the first image of the stitching body position may be display in an interface such as a stitching planning interface in step 220; and at least one region of interest of the stitching body position may be determined on the first image of the stitching body position in step 220.

In some embodiments, the travel point and X-ray exposure area related to the region of interest may be calculated according to the at least one region of interest determined on the first image in step 230, so that any region of interest can be fully covered by one of the individual X-ray exposure areas and said X-ray exposure area can fully cover the stitching area for stitching.

In some embodiments, the first image may include a depth-sensing image with three-dimensional spatial information about the stitching body position. In some embodiments, spatial coordinates corresponding to the region of interest may be obtained according to the at least one region of interest from the depth-sensing image, and the travel points and X-ray exposure area both associated with the region of interest may be calculated based on the spatial coordinates, so that any region of interest can be completely covered by one of the individual X-ray exposure areas and that the X-ray exposure area can cover the stitching area for stitching.

In some embodiments, the first image may include an optical image with two-dimensional spatial information about the stitching body position. In some embodiments, in step 230, spatial coordinates corresponding to the region of interest may be obtained according to at least one region of interest determined in the optical image and a pre-established mapping relationship between the optical image and spatial coordinates, and calculate the travel points and the X-ray exposure areas both associated with the region of interest according to the spatial coordinates corresponding to the region of interest, so that any region of interest can be completely covered by one of the individual X-ray exposure areas and the X-ray exposure area also completely can cover the stitching area for stitching.

The radiographic parameter set may be obtained at least according to the travel point and X-ray exposure area related to the region of interest in step 230. In some embodiments, it may determine whether there is a gap area not covered by the X-ray exposure areas of the region of interest in the stitching body position according to the travel points and the X-ray exposure areas both associated with the region of interest in step 230. When there is the gap area not be covered, the gap area may be obtained, as well as a travel point and an X-ray exposure area both associated with the gap area, which can be fully covered the gap area without overlapping with any region of interest in step 230; and the radiographic parameter set may be obtained according to the travel point and the X-ray exposure area both associated with the region of interest and the travel point and the X-ray exposure area both associated with the gap area in step 230. When there isn't the gap area not be covered, the radiographic parameter set may be obtained according to the travel points and the X-ray exposure areas both associated with the region of interest in step 230.

The above is based on the description of obtaining the region of interest on the first image and further obtaining the radiographic parameter set.

In some embodiments, when receiving a trigger instruction to calibrate a region of interest, the travel points of the X-ray source 10 and the irradiation field of the X-ray beam limiter 15 under the trigger instruction may be acquired to calibrate at least one region of interest of the stitching body position in step 220. In some embodiments, a region corresponding to the irradiation field of the X-ray beam limiter 15 may be taken as the region of interest in step 220. In some embodiments, a point of interest of the stitching body position may be determined according to the irradiation field of the X-ray beam limiter 15 under the trigger instruction, and then the region of interest may be determined based on the point of interest, for example, taking a region of preset size centered on the point of interest as the region of interest. In some embodiments, the length of the region of preset size in the first direction, for example, the direction of the coronal axis or the direction of the sagittal axis is less than a first threshold. In some embodiments, the length of the region of preset size in the second direction, for example, the direction of the vertical axis is less than a second threshold. In some embodiments, the first threshold is 27 cm to 25 cm. In some embodiments, the second threshold is 9 cm to 7 cm.

After obtaining the region of interest, the following describes how to determine the radiographic parameter set for the stitching body position.

In some embodiments, the travel points of the X-ray source 10 under the trigger instruction may be taken as the travel points related to the region of interest, and the irradiation field of the X-ray beam limiter 15 under the trigger instruction may be taken as the X-ray exposure area related to the region of interest in step 230; then the radiographic parameter set may be obtained at least according to the travel point and X-ray exposure area related to the region of interest. In some embodiments, it may determine whether there is a gap area not covered by the X-ray exposure area related to the region of interest according to the travel point and X-ray exposure area related to the region of interest in step 230. When there is the gap area not covered, the gap area, as well as the travel point and the X-ray exposure area both associated with the gap area may be obtained, so as to completely cover the gap area without overlapping with any region of interest in step 230; and the radiographic parameter set may be obtained based on the travel point and the X-ray exposure area both associated with the region of interest and the travel point and the X-ray exposure area both associated with the gap area in step 230. When there is no gap area not covered, the radiographic parameter set may be obtained based on the travel point and X-ray exposure area both associated with the region of interest in step 230.

In some implementations, it may also be possible to select images from the history of images that have been taken for stitching in the first direction.

Figure 17:
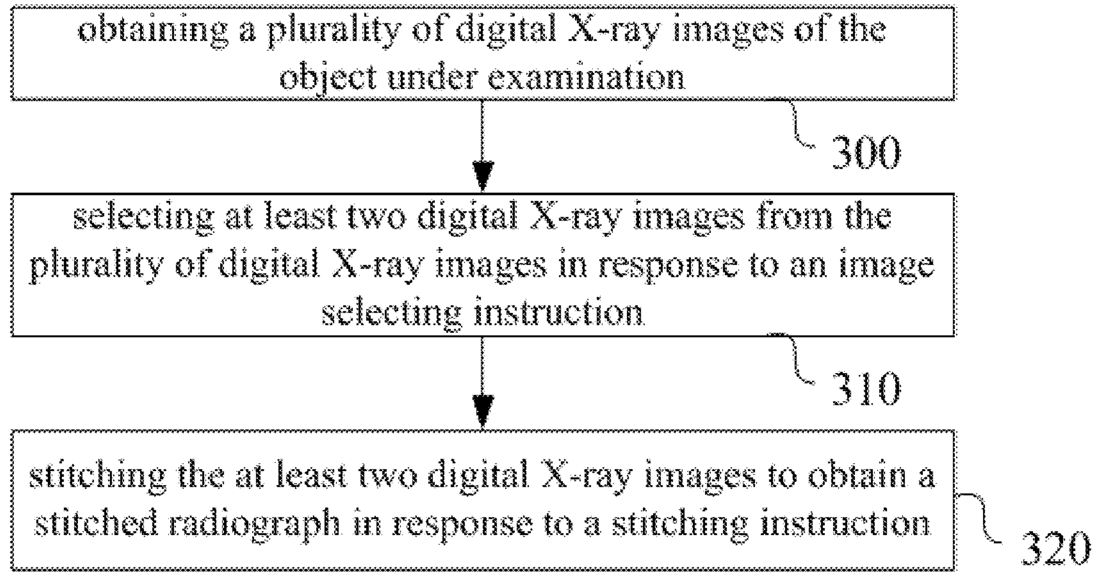
FIG. 17 is a flowchart of a digital X-ray imaging method in some embodiments.

Referring to FIG. 17, the digital X-ray imaging method in some embodiments may include the following steps:

Step 300: obtaining a plurality of digital X-ray images of the object under examination;

Step 310: selecting at least two digital X-ray images from the plurality of digital X-ray images in response to an image selecting instruction. The at least two digital X-ray images may have an overlapping area, for example, the plurality of digital X-ray images may be obtained after radiographing, and then be displayed by the display member 50 so that the at least two digital X-ray images that are required can be selected by a user with a tool such as a mouse.

Step 320: stitching the at least two digital X-ray images to obtain a stitched radiograph in response to a stitching instruction.

In some embodiments, stitching parameters at least comprising at least one of width, brightness, contrast, sharpness, compression ratio, and compensation factor of the stitching area may also be obtained; accordingly, the at least two digital X-ray images may be stitched based on the stitching parameters.

In some embodiments, in step 320, the region of interest in the at least two digital X-ray images may be acquired, and whether there is an overlap between the region of interest and the stitching area may be determined, and when there is the overlap, a prompt may be issued. The acquisition of the region of interest is described above and will not be repeated here.

In some embodiments, the digital X-ray imaging method may also include: display the at least two digital X-ray images and the stitched radiograph simultaneously.

The present disclosure has been illustrated by reference to various exemplary embodiments. However, those skilled in the art will recognize that the exemplary embodiments can be changed and modified without departing from the scope of the present disclosure. For example, the various operational steps and the components used to perform the operational steps can be implemented in different ways depending on a particular application or taking into account any number of cost functions associated with the operation of the system (for example, one or more steps can be deleted, modified or combined into other steps).

In the embodiments above, this may be accomplished, in whole or in part, by software, hardware, firmware, or any combination thereof. Furthermore, as will be understood by those skilled in the art, the principles of the present disclosure may be embodied in computer program products on computer readable storage media that are preloaded with computer readable program code. Any tangible, non-transitory computer readable storage media may be used, including magnetic storage devices (hard disks, floppy disks, etc.), optical storage devices (CD to ROM, DVD, Blu Ray disks, etc.), flash memory and/or the like. These computer program instructions may be loaded onto a general purpose computer, a special purpose computer, or other programmable data processing device to form a machine so that the instructions executed on the computer or other programmable data processing device generate a device for achieving a specified function. These computer program instructions may also be stored in computer readable memory that may instruct the computer or other programmable data processing device to operate in a particular manner so that the instructions stored in the computer readable memory form a manufactured article including an implementing device for achieving a specified function." A computer program instruction may also be loaded into a computer or other programmable data processing device so as to cause a series of operation steps to be executed on the computer or other programmable device to produce a computer-implemented process, so that the instructions executed on the computer or other programmable device provide the steps for implementing a specified function.

Although the principles of the present disclosure have been shown in various embodiments, many modifications of the structure, arrangement, proportions, elements, materials and parts particularly suited to particular environmental and operational requirements may be used without departing from the principles and scope of this disclosure. The above modifications and other changes or modifications will be included within the scope of this disclosure.

The foregoing specific descriptions have been described with reference to various embodiments. However, those skilled in the art will recognize that various modifications and changes can be made without departing from the scope of this disclosure. Therefore, the consideration of this disclosure will be in an illustrative rather than a restrictive sense and all such modifications will be included within its scope. Also, the advantages, other advantages and solutions to problems with respect to various embodiments have been described above. However, neither the benefits, advantages, solutions to problems nor any elements that generate them or make them more explicit should be construed as critical, necessary or required. The term "include" as used herein, and any other variation thereof, is used non-exclusively so that a process, method, article or device including a list of elements includes not only those elements but also other elements that are not expressly listed or not incorporated into the process, method, system, article or device. Further, the term "couple" as used herein, and any other variation thereof, refers to physical connection, electrical connection, magnetic connection, optical connection, communication connection, functional connection and/or any other connection.

Those skilled in the art will realize that many changes in the details of the above embodiments can be made without departing from the basic principles of the present disclosure. Therefore, the scope of the present disclosure should be determined only by the claims.

The invention claimed is:

1. A method of digital X-ray imaging, comprising:

displaying a detectable body part of an object under examination on a display interface;

determining a to-be-examined body position of the object from the detectable body part in response to a selection instruction on the detectable body part, the to-be-examined body position comprising a stitching body position, the stitching body position being radiographed in a first direction to obtain a plurality of digital X-ray images, the digital X-ray images being stitched to generate a radiograph of the stitching body position and to form a stitching area between adjacent digital X-ray images when stitching, and the first direction being a direction of a coronal axis or a sagittal axis of the object under examination;

acquiring at least one region of interest of the stitching body position;

determining a radiographic parameter set of the stitching body position, the radiographic parameter set comprising a plurality of travel points of an X-ray source and radiographic parameters about the X-ray source at the travel points, the at least one region of interest being captured during the digital X-ray imaging and kept outside the stitching area by using the radiographic parameter set;

in response to a radiographing instruction on the stitching body position, controlling the X-ray source to move to the travel points along the first direction based on the radiographic parameter set, and emitting X-rays to the stitching body position for radiographing based on the radiographic parameters about the X-ray source at the travel points to obtain the digital X-ray images; and stitching the digital X-ray images in the first direction to obtain the radiograph of the stitching body position;

wherein the acquiring at least one region of interest of the stitching body position comprises:

when receiving a trigger instruction to calibrate the region of interest, acquiring a travel point of the X-ray source and an irradiation field of an X-ray beam limiter under the trigger instruction; and taking a region corresponding to the irradiation field of the X-ray beam limiter as the region of interest, or determining a point of interest of the stitching body position according to the irradiation field of the X-ray beam limiter under the trigger instruction, and determining the region of interest based on the point of interest.

2. The method according to claim 1, wherein the stitching body position is a chest stitching position or an abdomen stitching position.

3. The method according to claim 1, further comprising: in response to the radiographing instruction on the stitching body position, controlling a detector to move based on the radiographic parameter set to receive the X-rays emitted at the travel points by the X-ray source to obtain the digital X-ray images; or receiving the X-rays emitted at the travel points by the X-ray source via a fixed detector to obtain the digital X-ray images.

4. The method according to claim 1, wherein determining the radiographic parameter set of the stitching body position comprises: determining the radiographic parameter set of the stitching body position based on the at least one region of interest.

5. The method according to claim 1, wherein the acquiring at least one region of interest of the stitching body position further comprises:

displaying a first image of the stitching body position on the display interface; and in response to a user operation, determining the at least one region of interest of the stitching body position on the first image of the stitching body position.

6. The method according to claim 5, wherein the determining the radiographic parameter set of the stitching body position comprises:

according to the at least one region of interest determined on the first image, calculating a travel point and an X-ray exposure area associated with the at least one region of interest, the at least one region of interest being covered by the X-ray exposure area which covers the stitching area for stitching; and acquiring the radiographic parameter set at least according to the travel point and the X-ray exposure area associated with the at least one region of interest.

7. The method according to claim 1, wherein the determining the radiographic parameter set of the stitching body position comprises:

respectively taking the travel point of the X-ray source and the irradiation field of the X-ray beam limiter under the trigger instruction as a travel point and an X-ray exposure area associated with the at least one region of interest; and acquiring the radiographic parameter set at least according to the travel point and the X-ray exposure area associated with the at least one region of interest.

8. The method according to claim 6, wherein the acquiring the radiographic parameter set at least according to the travel point and the X-ray exposure area associated with the at least one region of interest comprises:

according to the travel point and the X-ray exposure area associated with the at least one region of interest, determining whether a gap area at the stitching body position is not covered by the X-ray exposure area associated with the at least one region of interest, and acquiring the gap area when determining that the gap area exists;

determining a travel point and an X-ray exposure area associated with the gap area, to cover the gap area without overlapping with the at least one region of interest;

acquiring the radiographic parameter set according to the travel point and the X-ray exposure area associated with the at least one region of interest and the travel point and the X-ray exposure area associated with the gap area; and when determining that the gap area does not exist, acquiring the radiographic parameter set according to the travel point and the X-ray exposure area associated with the at least one region of interest.

9. A method of digital X-ray imaging, comprising:

configuring a current digital imaging mode in response to a mode configuring instruction, the current digital imaging mode comprising at least two of a first stitching mode, a second stitching mode and a third stitching mode, wherein the first stitching mode comprises radiographing a stitching body position along a direction of a coronal axis of an object under examination to obtain a plurality of digital X-ray images that are stitched to generate a radiograph of the stitching body position, the second stitching mode comprises radiographing the stitching body position along a direction of a sagittal axis of the object under examination to obtain a plurality of digital X-ray images that are stitched to generate the radiograph of the stitching body position, and the third stitching mode comprises radiographing the stitching body position along a direction of a vertical axis of the object under examination to obtain a plurality of digital X-ray images that are stitched to generate the radiograph of the stitching body position;

when the current digital imaging mode is the first stitching mode:

controlling an X-ray source to emit X-rays to the stitching body position of the object under examination to obtain the digital X-ray images in the direction of the coronal axis; and stitching the digital X-ray images along the direction of the coronal axis to obtain the radiograph of the stitching body position;

when the current digital imaging mode is the second stitching mode:

controlling the X-ray source to emit X-rays to the stitching body position of the object under examination to obtain the digital X-ray images in the direction of the sagittal axis; and stitching the digital X-ray images along the direction of the sagittal axis to obtain the radiograph of the stitching body position; and when the current digital imaging mode is the third stitching mode:

controlling the X-ray source to emit X-rays to the stitching body position of the object under examination to obtain the digital X-ray images in the direction of the vertical axis; and stitching the digital X-ray images along the direction of the vertical axis to obtain the radiograph of the stitching body position;

wherein the digital X-ray images are obtained based on a radiographic parameter set of the stitching body position, the radiographic parameter set of the stitching body position is determined based on at least one region of interest, and the method further comprises: acquiring the at least one region of interest of the stitching body position, comprising:

when receiving a trigger instruction to calibrate the region of interest, acquiring a travel point of the X-ray source and an irradiation field of an X-ray beam limiter under the trigger instruction; and taking a region corresponding to the irradiation field of the X-ray beam limiter as the region of interest, or determining a point of interest of the stitching body position according to the irradiation field of the X-ray beam limiter under the trigger instruction, and determining the region of interest based on the point of interest.

10. The method according to claim 9, wherein the current digital imaging mode further comprises a fourth stitching mode, wherein the fourth stitching mode comprises: radiographing the stitching body position along at least two directions of the object under examination to obtain a plurality of digital X-ray images that are stitched to generate the radiograph of the stitching body position, the at least two directions include at least two of the coronal axis, the direction of the sagittal axis, and the direction of the vertical axis of the object under examination; and when the current digital imaging mode is the fourth stitching mode:

controlling the X-ray source to emit X-rays to the stitching body position of the object under examination to obtain a plurality of digital X-ray images in the at least two directions; and stitching the digital X-ray images along the at least two directions to obtain the radiograph of the stitching body position.

11. The method according to claim 10, wherein the digital X-ray images in the at least two directions comprise a plurality of digital X-ray images in the direction of the coronal axis and a plurality of digital X-ray images in the direction of the vertical axis; and stitching the digital X-ray images along the at least two directions to obtain the radiograph of the stitching body position comprises:

stitching the digital X-ray images in the direction of the coronal axis along the direction of the coronal axis to obtain an intermediate stitching image, and stitching the intermediate stitching image and the digital X-ray images in the direction of the vertical axis along the direction of the vertical axis to obtain the radiograph of the stitching body position; or stitching the digital X-ray images in the direction of the vertical axis along the direction of the vertical axis to obtain an intermediate stitching image, and stitching the intermediate stitching image and the digital X-ray images in the direction of the coronal axis along the direction of the coronal axis to obtain the radiograph of the stitching body position.

12. The method according to claim 9, further comprising: switching among the current digital imaging mode in response to a triggering of a mode switching button.

13. A digital X-ray imaging apparatus, comprising:

an X-ray source configured to emit X-rays to an object under examination;

a detector configured to receive the X-rays penetrating the object under examination;

a driving member configured to drive the X-ray source and/or the detector to move; and a processor configured to execute the method according to claim 1.

14. A digital X-ray imaging method, comprising:

controlling an X-ray source to emit X-rays to a stitching body position of an object under examination based on a radiographic parameter set, receiving the X-rays penetrating the stitching body position via a single detector to obtain a plurality of digital X-ray images in at least two directions respectively; and stitching the digital X-ray images along the at least two directions to obtain a radiograph of the stitching body position;

wherein the radiographic parameter set of the stitching body position is determined based on at least one region of interest, and the method further comprises:

acquiring the at least one region of interest of the stitching body position, comprising:

when receiving a trigger instruction to calibrate the region of interest, acquiring a travel point of the X-ray source and an irradiation field of an X-ray beam limiter under the trigger instruction; and taking a region corresponding to the irradiation field of the X-ray beam limiter as the region of interest, or determining a point of interest of the stitching body position according to the irradiation field of the X-ray beam limiter under the trigger instruction, and determining the region of interest based on the point of interest.

15. The method according to claim 14, wherein the digital X-ray images in the at least two directions comprise a plurality of digital X-ray images along a direction of a coronal axis and a plurality of digital X-ray images along a direction of a sagittal axis, or the digital X-ray images in the direction of the coronal axis and a plurality of digital X-ray images in a direction of a vertical axis, or the digital X-ray images in the direction of the sagittal axis and the digital X-ray images in the direction of the vertical axis.

* * * * *